United States Patent
Yoshikawa et al.

(10) Patent No.: US 6,911,595 B2
(45) Date of Patent: Jun. 28, 2005

(54) CHARGE TRANSFER MATERIAL, AND PHOTOELECTRIC CONVERSION DEVICE AND PHOTOELECTRIC CELL USING SAME, AND PYRIDINE COMPOUND

(75) Inventors: Masaru Yoshikawa, Kanagawa-ken (JP); Chang-yi Qian, Kanagawa-ken (JP)

(73) Assignee: Fuji Photo Film Co., Ltd., Minami-Ashigara (JP)

(*) Notice: Subject to any disclaimer, the term of this patent is extended or adjusted under 35 U.S.C. 154(b) by 209 days.

(21) Appl. No.: 10/170,504

(22) Filed: Jun. 14, 2002

(65) Prior Publication Data

US 2003/0127129 A1 Jul. 10, 2003

(30) Foreign Application Priority Data

Jun. 14, 2001 (JP) ........................................ 2001-180427

(51) Int. Cl.[7] ........................ H01L 31/04; H01L 31/06; C07D 213/81
(52) U.S. Cl. ........................ 136/263; 136/256; 429/111; 429/206; 429/207; 429/188; 429/324; 429/213; 252/62.2; 252/501.1; 252/500; 546/304; 546/307; 546/312; 548/326.5; 548/331.5; 548/332.5; 564/96; 564/98
(58) Field of Search ................................ 136/263, 256; 429/111, 206, 207, 188, 324, 213; 252/62.2, 501.1, 500; 546/304, 307, 312; 548/326.5, 331.5, 332.5; 564/96, 98

(56) References Cited

U.S. PATENT DOCUMENTS

| | | | | |
|---|---|---|---|---|
| 6,120,696 A | * | 9/2000 | Armand et al. | 252/62.2 |
| 6,171,522 B1 | * | 1/2001 | Michot et al. | 252/500 |
| 6,228,942 B1 | * | 5/2001 | Michot et al. | 525/183 |
| 6,319,428 B1 | * | 11/2001 | Michot et al. | 252/500 |
| 6,333,425 B1 | * | 12/2001 | Michot et al. | 558/167 |
| 6,365,068 B1 | * | 4/2002 | Michot et al. | 252/500 |
| 6,365,301 B1 | * | 4/2002 | Michot et al. | 429/307 |
| 6,384,321 B1 | * | 5/2002 | Mikoshiba et al. | 136/263 |
| 6,395,367 B1 | * | 5/2002 | Michot et al. | 428/64.8 |
| 6,576,159 B1 | * | 6/2003 | Michot et al. | 252/511 |
| 6,620,546 B1 | * | 9/2003 | Michot et al. | 429/188 |
| 6,750,352 B2 | * | 6/2004 | Ono et al. | 548/341.5 |

(Continued)

FOREIGN PATENT DOCUMENTS

| | | |
|---|---|---|
| EP | 0718288 A1 | 12/1995 |
| EP | 850920 A2 * | 7/1998 |
| EP | 0850933 A1 | 7/1998 |
| EP | 850933 A1 * | 7/1998 |
| EP | 1075005 A2 | 2/2001 |
| EP | 1 089 305 A2 | 4/2001 |
| WO | WO 99/28292 A1 * | 6/1999 |
| WO | WO99/28292 A1 | 6/1999 |

OTHER PUBLICATIONS

Search Report issued in European Patent Application No. EP 02 01 3176, Apr. 14, 2004.

*Primary Examiner*—Alan Diamond
(74) *Attorney, Agent, or Firm*—Burns, Doane, Swecker & Mathis, L.L.P.

(57) ABSTRACT

A charge transfer material comprising a basic compound having negative charge and represented by the following general formula (I):

$$(A_1\text{-}L)_{n1}\text{-}A_2\cdot M \qquad (I),$$

wherein $A_1$ represents a group having negative charge; $A_2$ represents a basic group; M represents a cation for neutralizing the negative charge of $(A_1\text{-}L)_{n1}\text{-}A_2$; L represents a divalent linking group or a single bond; and n1 represents an integer of 1 to 3. A photoelectric conversion device and a photo-electrochemical cell comprising the charge transfer material. A new nonvolatile pyridine compound, which is a low-viscosity liquid at room temperature, is preferably used for $A_2$.

8 Claims, 5 Drawing Sheets

U.S. PATENT DOCUMENTS

| | | | |
|---|---|---|---|
| 2001/0024749 A1 * | 9/2001 | Michot et al. | 429/122 |
| 2002/0009635 A1 * | 1/2002 | Michot et al. | 429/188 |
| 2002/0009650 A1 * | 1/2002 | Michot et al. | 429/314 |
| 2002/0034690 A1 * | 3/2002 | Ono | 429/306 |
| 2002/0040728 A1 * | 4/2002 | Yoshikawa | 136/263 |
| 2002/0055045 A1 * | 5/2002 | Michot et al. | 429/307 |
| 2002/0102380 A1 * | 8/2002 | Michot et al. | 428/64.8 |
| 2003/0052310 A1 * | 3/2003 | Michot et al. | 252/500 |
| 2003/0066988 A1 * | 4/2003 | Michot et al. | 252/500 |

* cited by examiner

CHARGE TRANSFER MATERIAL, AND PHOTOELECTRIC CONVERSION DEVICE AND PHOTOELECTRIC CELL USING SAME, AND PYRIDINE COMPOUND

FIELD OF THE INVENTION

The present invention relates to a charge transfer material, a photoelectric conversion device having a charge transfer layer comprising such a charge transfer material and a layer comprising fine semiconductor particles sensitized by a dye, and a photoelectric cell comprising the photoelectric conversion device. The present invention also relates to a pyridine compound that is in a liquid state at room temperature.

BACKGROUND OF THE INVENTION

Photoelectric conversion devices are used for various kinds of optical sensors, copiers, photoelectric generators, etc. Put into practical use are various types of photoelectric conversion devices, such as those using metals, those using semiconductors, those using organic pigments or dyes, combinations thereof.

"Nature," Vol. 353, pages 737 to 740 (1991), U.S. Pat. No. 4,927,721, etc. disclose photoelectric conversion devices utilizing fine semiconductor particles sensitized by dyes, and solar cells comprising them. A photoelectric conversion device comprising fine semiconductor particles sensitized by a dye is referred to as a dye-sensitized photoelectric conversion device hereinafter. Electrolytic solutions comprising iodine salts are used in the dye-sensitized photoelectric conversion devices as charge transfer materials. Further known is a photoelectric conversion device in which a molten electrolytic salt comprising an imidazolium salt, a low-melting point compound, is used as a charge transfer material to prevent the leakage and depletion of an electrolytic solution, and thus to improve the durability of the photoelectric conversion device (WO 95/18456). However, a photoelectric conversion device comprising this charge transfer material as a charge transfer layer does not necessarily have sufficiently high photoelectric conversion efficiency. Further improvement of the photoelectric conversion efficiency is thus desired.

It is known that the photoelectric conversion efficiency of a photoelectric conversion device is improved by adding a basic compound such as 4-t-butylpyridine or lithium iodide, etc. to a charge transfer material. However, because a basic compound such as 4-t-butylpyridine is generally a volatile liquid, such a photoelectric conversion device is disadvantageous in durability for a long-term operation. Known as a nonvolatile basic compound usable for the charge transfer material is a polymer having a basic group. However, because such a polymer is solid or liquid at room temperature, a charge transfer material comprising this polymer is highly viscous, resulting in drastic decrease in charge transportability.

On the other hand, known as a means for turning a compound nonvolatile without increasing its molecular weight is a method for introducing a charged group into the compound. For instance, JP 2001-167630 A discloses the use of a compound whose positive-charge group such as an imidazolium group, a pyridinium group, etc. is substituted by a basic group such as a pyridyl group, etc. as a charge transfer material. However, there has been no known example of using a basic compound having negative charge as a charge transfer material. Most of such known basic compounds having charge are not liquid at room temperature, and even if they are liquid, they have extremely high viscosity. Accordingly, their addition to the charge transfer layer results in decrease in charge transportability as in the case of the above polymer. Under these circumstances, it is strongly desired to develop a nonvolatile basic compound, which is a low-viscosity liquid at room temperature.

OBJECT OF THE INVENTION

An object of the present invention is to provide a charge transfer material excellent in charge transportability and durability.

Another object of the present invention is to provide a dye-sensitized photoelectric conversion device comprising a charge transfer material for exhibiting excellent photoelectric conversion efficiency and stability during a long-term operation.

A further object of the present invention is to provide a photoelectric cell comprising the dye-sensitized photoelectric conversion device.

A still further object of the present invention is to provide a nonvolatile pyridine compound, which is low-viscosity liquid at room temperature.

SUMMARY OF THE INVENTION

The charge transfer material of the present invention comprises a basic compound having negative charge and represented by the following general formula (I):

$$(A_1\text{-}L)_{n1}\text{-}A_2\cdot M \qquad (I),$$

wherein $A_1$ represents a group having negative charge; $A_2$ represents a basic group; M represents a cation for neutralizing the negative charge of $(A_1\text{-}L)_{n1}\text{-}A_2$; L represents a divalent linking group or a single bond; and n1 represents an integer of 1 to 3.

The photoelectric conversion device of the present invention comprises a conductive support, a layer of dye-adsorbed, fine semiconductor particles, a charge transfer layer and a counter electrode, the charge transfer layer comprising the charge transfer material of the present invention.

The photoelectric cell of the present invention comprises the photoelectric conversion device of the present invention.

With the following conditions satisfied, further improvement is achieved in the durability and charge transportability of the charge transfer material, and in the durability and photoelectric conversion efficiency of the photoelectric conversion device and the photoelectric cell.

(1) In the general formula (I), $A_1$ preferably comprises $N^-$.
(2) In the general formula (I), $A_2$ is preferably a pyridyl group, an imidazolyl group or an amino group.
(3) In the general formula (I), M is preferably an alkali metal cation, an alkaline earth metal cation, a quaternary ammonium cation, an imidazolium cation or a pyridinium cation.
(4) In the general formula (I), it is particularly preferable that $A_1$ is $R_1SO_2N^-$—, wherein $R_1$ represents an alkyl group having at least one fluorine substituent; $A_2$ is a pyridyl group; M is a lithium cation or an imidazolium cation; L is a single bond; and n1 is 1.
(5) The above basic compound is preferably in a molten state at room temperature.
(6) The charge transfer material preferably comprises an alkali metal salt and/or an alkaline earth metal salt.

(7) The charge transfer material preferably comprises an iodine salt and/or iodine.
(8) The charge transfer material is preferably in a liquid state at room temperature.
(9) In the photoelectric conversion device, the layer of fine semiconductor particles is preferably treated with a ureide compound and/or a silyl compound.
(10) An alkali metal salt and/or an alkaline earth metal salt is preferably added to the dye solution for causing fine semiconductor particles to adsorb a dye.
(11) The dye adsorbed onto the fine semiconductor particles is preferably a ruthenium complex dye.

The charge transfer material of the present invention preferably comprises as a basic compound having negative charge a pyridine compound represented by the following general formula (II):

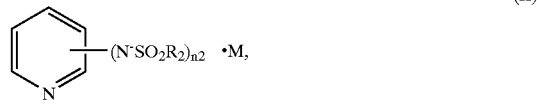

(II)

wherein $R_2$ represents an alkyl group having at least one fluorine substituent; M represents an alkaline earth metal cation, a quaternary ammonium cation, an imidazolium cation or a pyridinium cation; and n2 represents an integer of 1 to 3. M is preferably an imidazolium cation. The pyridine compound represented by the general formula (II) is in a molten state at room temperature.

DETAILED DESCRIPTION OF THE PREFERRED EMBODIMENTS

[1] Charge Transfer Material

Figure 1:
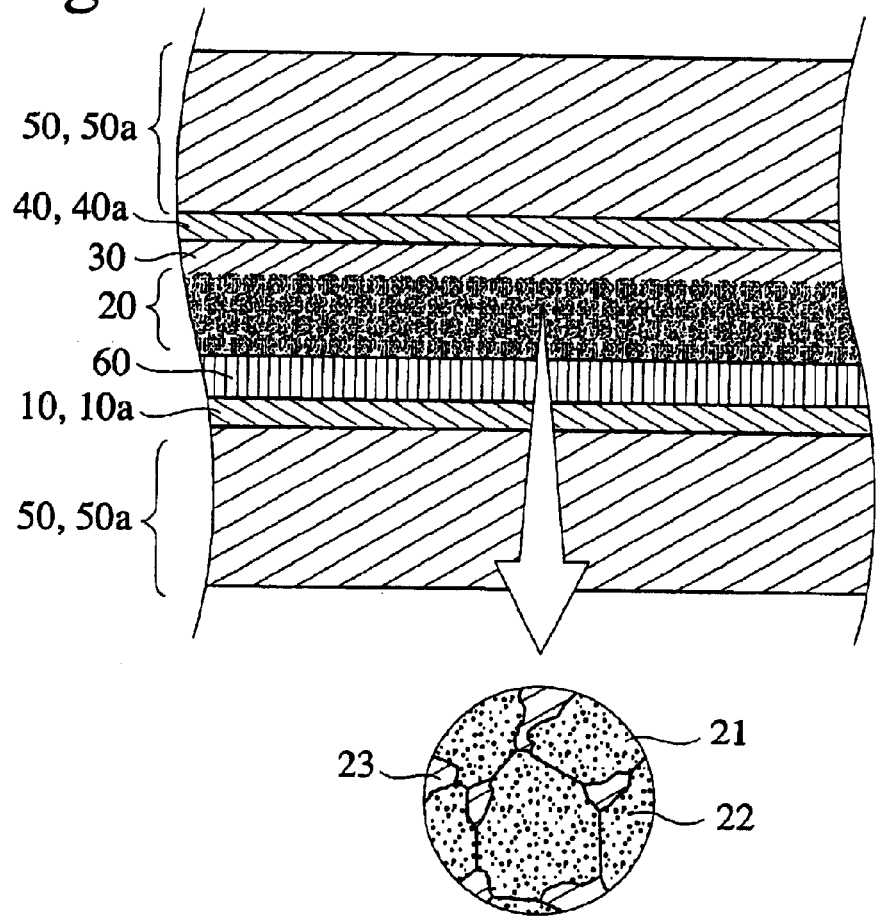
FIG. 1 is a partial cross sectional view showing a preferable structure of the photoelectric conversion device of the present invention.

The charge transfer material of the present invention comprising a basic compound having negative charge is usable for a solvent for chemical reactions, metal plating, etc., CCD (charge-coupled device) cameras, various photoelectric conversion devices, cells, etc.

(A) Basic Compound

The "basic compound" in the present invention is a compound having at least one basic group. The term "basic group" used herein means a group that provides, if a hydrogen atom is added, a compound whose conjugate acid exhibits pKa of 3 to 15. The pKa is a value measured in a mixed solvent of tetrahydrofuran (THF) and water (THF:water=1:1) at 25° C. The basic compound used in the present invention has negative charge, whose valence is not particularly limited. The negative charge may exist locally or throughout the compound. It is preferable that the basic compound used in the present invention is in a molten state at room temperature. The term "room temperature" used herein means 25° C.

The basic compound having negative charge used in the charge transfer material of the present invention is represented by the following general formula (I). The basic compound represented by the general formula (I) is referred hereinafter to as "basic compound (I)."

(I).

In the general formula (I), $A_1$ represents a group having negative charge. Examples of $A_1$ include groups having negative charge on an oxygen atom, such as $—SO_3^-$, $—CO_2^-$, $—PO_3^{2-}$ and $—O^-$, groups having negative charge on a nitrogen atom, such as $RSO_2N^-—$, $RSO_2N^-SO_2—$, $RCON^-—$, $RCON^-CO—$, $RSO_2N^-CO—$, $RR'PON^-—$ and $RR'PON^-CO—$, groups having negative charge on a sulfur atom, such as $—SO_2S^-$, $—S(=O)_2^-$ and $—S^-$, groups having negative charge on a carbon atom, such as $RCOCH^-CO—$; and groups having negative charge on a phosphorus atom such as $RCOP^-—$. As described above, the negative charge may be localized or not localized. Preferable among them are groups having negative charge on a nitrogen atom, in which $A_1$ comprises $N^-$. $A_1$ is more preferably $RSO_2N^-—$, $RSO_2N^-SO_2—$, $RCON^-—$, $RCON^-CO—$ or $RSO_2N^-CO—$, particularly $RSO_2N^-—$.

The above R and R' independently represent a hydrogen atom or a substituent. R and R' may be the same or different. Examples of such substituent include an aliphatic hydrocarbon group, an aryl group, a heterocyclic group, an amino group, a hydroxy group, an alkyloxy group, etc.

Examples of the aliphatic hydrocarbon groups represented by each of R and R' include unsubstituted alkyl groups having 1 to 18 carbon atoms, which may be straight or branched, such as a methyl group, an ethyl group, i-propyl group, an n-propyl group, an n-butyl group, a t-butyl group, a 2-pentyl group, an n-hexyl group, an n-octyl group, t-octyl group, a 2-ethylhexyl group, a 1,5-dimethylhexyl group, an n-decyl group, an n-dodecyl group, an n-tetradecyl group, an n-hexadecyl group and an n-octadecyl group; substituted alkyl groups having 1 to 18 carbon atoms, which may be straight or branched, such as a trifluoromethyl group, a trifluoroethyl group, a tetrafluoroethyl group, a pentafluoroethyl group, a perfluorobutyl group, a methoxycarbonylmethyl group, an n-butoxypropyl group, a methoxyethoxyethyl group, a polyethoxyethyl group, an acetyloxyethyl group, a methylthiopropyl group, a 3-(N-ethylureide)propyl group; substituted or unsubstituted, cyclic alkyl groups having 3 to 18 carbon atoms such as a cyclopropyl group, a cyclopentyl group, a cyclohexyl group, a cyclooctyl group, an adamantyl group and a cyclododecyl group; alkenyl groups having 2 to 16 carbon atoms such as an allyl group, a 2-butenyl group and a 3-pentenyl group; alkynyl groups having 2 to 10 carbon atoms such as a propargyl group and a 3-pentynyl group; aralkyl groups having 6 to 16 carbon atoms such as a benzyl group, etc.

Examples of the aryl groups represented by each of R and R' include substituted or unsubstituted phenyl groups having 6 to 20 carbon atoms such as a phenyl group, a methylphenyl group, an octylphenyl group, a cyanophenyl group, an ethoxycarbonylphenyl group, a trifluoromethylphenyl group, a pentafluorophenyl group, a carbomethoxyphenyl group and a butoxyphenyl group; substituted or unsubstituted naphthyl groups such as a naphthyl group and a 4-sulfonaphthyl group; etc.

Examples of the heterocyclic groups represented by each of R and R' include substituted or unsubstituted, 5-membered, nitrogen-containing heterocycle groups; substituted or unsubstituted, 6-membered, nitrogen-containing heterocycle groups such as a triazino group; and a furyl group; a thiofuryl group, etc.

Examples of the amino groups represented by each of R and R' include a dimethylamino group, etc.

Examples of the alkyloxy groups represented by each of R and R' include an ethyloxy group, a methyloxy group, etc.

Among them, each of R and R' is preferably a substituted or unsubstituted alkyl group, or a substituted or unsubstituted phenyl group, particularly an alkyl group having at least one fluorine substituent.

In the general formula (I), $A_2$ represents a basic group. A conjugated acid of a compound obtained by adding a hydrogen atom to $A_2$ exhibits pKa of 3 to 15, preferably 4 to 14, more preferably 5 to 13. Examples of the basic group include a pyridyl group, an imidazolyl group, an amino group, a guanidino group and a hydrazino group, etc. Preferable among them are a pyridyl group, an imidazolyl group and an amino group, particularly a pyridyl group. This basic group may comprise other substituents than $(A_1\text{-L})_{n1}\text{-}$.

In the general formula (I), M represents a cation for neutralizing the negative charge of $(A_1\text{-L})_{n1}\text{-}A_2$. Examples of the cation include alkali metal cations such as a lithium cation, a sodium cation, a potassium cation, a rubidium cation and a cesium cation; alkaline earth metal cations such as a magnesium cation, a calcium cation and a strontium cation; substituted or unsubstituted ammonium cations such as an unsubstituted ammonium cation, a triethylammonium cation, a tetramethylammonium cation, a tetra-n-butylammonium cation, a tetra-n-hexylammonium cation and an ethyltrimethylammonium cation; substituted or unsubstituted imidazolium cations such as a 1,3-dimethylimidazolium cation, a 1-ethyl-3-methylimidazolium cation, a 1-butyl-3-methylimidazolium cation and 2,3-dimethyl-1-propylimidazolium cation; substituted or unsubstituted pyridinium cations such as an N-methylpyridinium cation and a 4-phenylpyridinium cation; etc. M is preferably an alkali metal cation, an alkaline earth metal cation, a quaternary ammonium cation, an imidazolium cation or a pyridinium cation, more preferably an alkali metal cation or an imidazolium cation, particularly a lithium cation or a 1,3-dialkylimidazolium cation. It should be noted that M represents the type and number of the cation. For example, when the negative charge of $(A_1\text{-L})_{n1}\text{-}A_2$ has a total valence number of 1, and when the type of the cation is $Mg^{2+}$, M is "½($Mg^{2+}$)."

In the general formula (I), L represents a divalent linking group or a single bond. Examples of the divalent linking group include substituted or unsubstituted alkylene groups having 1 to 18 carbon atoms, which may be straight or branched, such as a methylene group, an ethylene group, a trimethylene group, a tetramethylene group, an isopropylene group and a tetrafluoroethylene group; oxyalkylene groups having 1 to 18 carbon atoms such as —$CH_2CH_2OCH_2CH_2$—, —$CH_2CH_2OCH_2CH_2OCH_2CH_2$—; alkyleneoxy groups and phenyleneoxy groups having 1 to 18 carbon atoms such as —$CH_2CH_2O$—, —$CH_2CH_2CH_2O$—, —$CH_2CH_2OCH_2CH_2O$— and -PhO—; alkyleneamino groups and phenyleneamino groups having 1 to 18 carbon atoms such as —$(CH_2CH_2)_2N$—, —$(OCH_2CH_2)_2N$— and -PhNH—; alkylenethio groups and phenylenethio groups having 1 to 18 carbon atoms such as —$CH_2CH_2S$—, —$CH_2CH_2CH_2S$—, —$CH_2CH_2OCH_2CH_2CH_2S$— and -PhS—; substituted or unsubstituted phenylene groups having 6 to 20 carbon atoms; sulfamoyl linking groups such as —$SO_2NH$—; carbamoyl linking groups such as —CONH—, amide linking groups such as —NHCO—; sulfonamide linking groups such as —$NHSO_2$—; ureide linking groups such as —NHCONH—; thioureide linking groups such as —NHCSNH—; urethane linking groups such as —OCONH—; thiourethane linking groups such as —OCSNH—; oxycarbonyl linking groups such as —OCO—; carbonyloxy linking groups such as —$CO_2$—; heterocycle linking groups; and combinations thereof, etc. L is preferably an alkylene group having 1 to 6 carbon atoms or a single bond, particularly a single bond.

In the general formula (I), n1 is the number of $(A_1\text{-L})$, which is an integer of 1 to 3. n1 is preferably 1.

In the general formula (I), it is preferable that $A_1$ represents a group having negative charge on a nitrogen atom, that $A_2$ represents a pyridyl group, an imidazolyl group or an amino group, that M represents an alkali metal cation or an imidazolium cation, that L is a single bond, and that n1 is 1. It is particularly preferable that $A_1$ is $R_1$ $SO_2N^-$—, wherein $R_1$ represents an alkyl group having at least one fluorine substituent, that $A_2$ is a pyridyl group, that M is a lithium cation or an imidazolium cation, that L is a single bond, and that n1 is 1.

Preferably used in the charge transfer material of the present invention as the above basic compound (I) is the pyridine compound represented by the following general formula (II). The pyridine compound represented by the general formula (II) is in a molten state at room temperature.

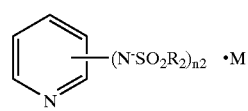

(II)

In the general formula (II), $R_2$ represents an alkyl group having at least one fluorine substituent; M represents an alkaline earth metal cation, a quaternary ammonium cation, an imidazolium cation or a pyridinium cation; and n2 represents an integer of 1 to 3. It is preferable that $R_2$ represents a trifluoromethyl group, and that M represents an imidazolium cation.

Examples of the basic compound (I) will be illustrated below without intention of restriction.

| | L | $A_1$ | M | $R_{10}$ | $R_{11}$ | $R_{12}$ | $R_{13}$ |
|---|---|---|---|---|---|---|---|
| b1-1 | — | $CF_3SO_2N^-$— | 1-methyl-3-ethylimidazolium | H | H | H | H |
| b1-2 | — | $CF_3CF_2SO_2N^-$— | $Li^+$ | H | H | H | H |
| b1-3 | — | $CF_3CON^-$— | 1-methyl-3-propylimidazolium | H | H | H | H |
| b1-4 | — | $CF_3SO_2N^-C(O)$— | 1-methyl-3-ethylimidazolium | H | H | H | H |
| b1-5 | — | $CH_3SO_2N^-$— | $Na^+$ | H | H | H | H |
| b1-6 | — | $NC\text{-}C_6H_4\text{-}SO_2N^-$— | $N^+(CH_2CH_2CH_2CH_3)_4$ | H | H | H | H |
| b1-7 | —$(CH_2)_3$— | $CF_3SO_2N^-$— | 1-octylpyridinium | $CH_3$ | H | H | H |
| b1-8 | — | $(CH_3CH_2O)_2P(O)N^-C(O)$— | $1/2(Mg^{2+})$ | H | H | H | H |
| b1-9 | — | tetrazole-5-thiolate | $Na^+$ | H | H | H | H |
| b1-10 | — | $CF_3SO_2N^-$— | 1,2-dimethyl-3-ethylimidazolium | H | Cl | H | H |
| b1-11 | — | $CF_3SO_2N^-C(O)$— | 1-methyl-3-ethylimidazolium | H | $CH_3O$ | H | H |
| b1-12 | —$O(CH_2)_4$—<br>(oxygen atom is bonded to pyridine ring) | $CF_3SO_2N^-SO_2$— | 1-methyl-3-ethylimidazolium | H | H | H | H |

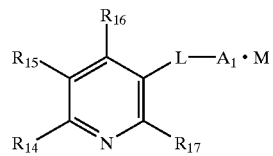

-continued
| | L | A₁ | M | R₁₄ | R₁₅ | R₁₆ | OR₁₇ |
|---|---|---|---|---|---|---|---|
| b2-1 | — | CF₃SO₂N⁻— | 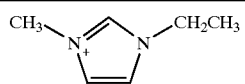 | H | H | H | H |
| b2-2 | — | CF₃SO₂N⁻— | 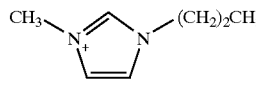 | H | H | H | H |
| b2-3 | — | CF₃SO₂N⁻— | Li⁺ | H | H | H | H |
| b2-4 | — | 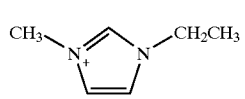 | 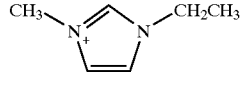 | H | H | H | H |
| b2-5 | — | 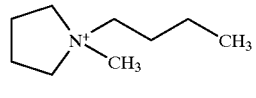 | 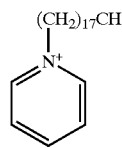 | H | H | H | H |
| b2-6 | — | CF₃CON⁻— | 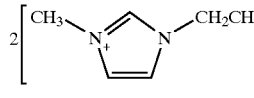 | H | H | H | H |
| b2-7 | —(CH₂)₃— | CF₃SO₂N⁻SO₂— | 1/2(Mg²⁺) | CH₃ | H | H | H |
| b2-8 | —(CH₂)₃— | —SO₃⁻ | 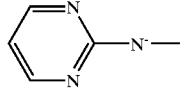 | H | H | H | H |
| b2-9 | — | CF₃SO₂N⁻— | 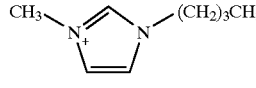 | H | CF₃SO₂N⁻— | H | H |
| b2-10 | — | 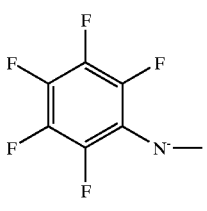 | 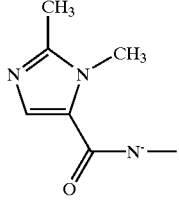 | H | H | H | H |
| b2-11 | — | 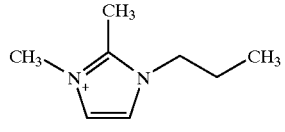 | Cs⁺ | H | H | H | H |
| b2-12 | — | 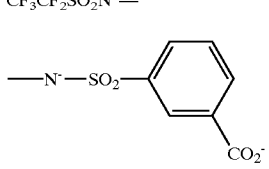 | 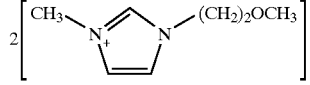 | H | H | H | H |
| b2-13 | — | CF₃CF₂SO₂N⁻— | Rb⁺ | H | H | H | H |
| b2-14 | — |  |  | H | H | H | H |

-continued

| | L | A₁ | M | R₁₈ | R₁₉ | R₂₀ | R₂₁ |
|---|---|---|---|---|---|---|---|
| b2-15 | — | CF₃SO₂N⁻— | 2[CH₃-N⁺(imidazole)-CH₂CH₃] | H | H | CF₃SO₂N⁻— | H |
| b2-16 | — | CF₃SO₂N⁻— | 2[CH₃-N⁺(imidazole)-CH₂CH₃] | CF₃SO₂N⁻— | H | H | H |
| b2-17 | — | CF₃SO₂N⁻— | CH₃-N⁺(imidazole)-CH₂CH₃ | H | H | Cl | H |
| b2-18 | — | CF₃SO₂N⁻CO— | CH₃-N⁺(imidazole)-CH₂CH₃ | H | H | CH₃CH₂O | H |
| b2-19 | — | CF₃SO₂N⁻CO— | CH₃-N⁺(imidazole)-CH₂CH₃ | H | —(CH₂)₄— | | H |

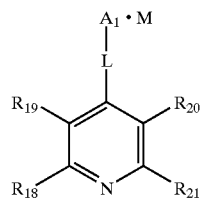

| | L | A₁ | M | R₁₈ | R₁₉ | R₂₀ | R₂₁ |
|---|---|---|---|---|---|---|---|
| b3-1 | — | CF₃SO₂N⁻— | CH₃-N⁺(imidazole)-(CH₂)₃CH₃ | H | H | H | H |
| b3-2 | —(CH₂)₃— | CF₃SO₂N⁻SO₂— | CH₃-N⁺(imidazole)-CH₂CH₃ | H | H | H | H |
| b3-3 | —OCH₂CH₂— | —SO₃⁻ | Li⁺ | H | H | H | H |
| b3-4 | — | CF₃CF₂SO₂N⁻C(=O)— | CH₃CH₂-N⁺(pyrazole)-CH₃ | H | H | H | H |
| b3-5 | —CH₂— | (CF₃CH₂O)₂P(=O)N⁻— | CH₃-N⁺(imidazole)-CH₂CH₃ | H | H | H | H |
| b3-6 | — | (CH₃)₂NS(=O)₂N⁻— | CH₃CH₂-N⁺(imidazole)-(CH₂)₂CH₃ | H | H | H | H |
| b3-7 | —SCH₂CH₂— | CF₃S(=O)N⁻SO₂(=O)— | Li⁺ | H | H | H | H |
| b3-8 | — | CF₃SO₂N⁻— | CH₃-N⁺(imidazole)-CH₂CH₃ | Cl | H | H | Cl |

-continued

| | | | | | | | | |
|---|---|---|---|---|---|---|---|---|
| b3-9 | — | CF$_3$SO$_2$N$^-$C(=O)— | 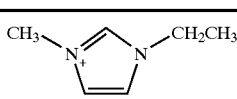 | CH$_3$O | H | H | CH$_3$O | |

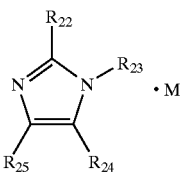

| | R$_{22}$ | R$_{23}$ | R$_{24}$ | R$_{25}$ | M |
|---|---|---|---|---|---|
| b4-1 | CF$_3$SO$_2$N$^-$— | CH$_3$— | H | H | 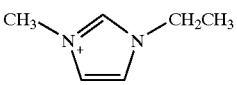 |
| b4-2 | H | CH$_3$CH$_2$— | CF$_3$SO$_2$N$^-$C(=O)— | H | Li$^+$ |
| b4-3 | H | CF$_3$SO$_2$N$^-$—(CH$_2$)$_3$— | H | H | Li$^+$ |
| b4-4 | H | CH$_3$— | H | CF$_3$SO$_2$N$^-$SO$_2$— | 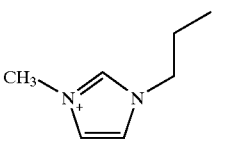 |
| b5-1 | 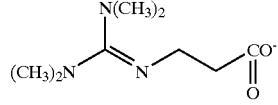 | | | | 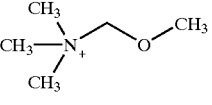 |
| b5-2 | 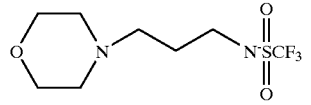 | | | | 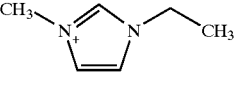 |

The basic compound (I) may easily be synthesized by a known method. For example, when A$_1$ is a group comprising N$^-$, the basic compound (I) can easily be formed with a high yield by a nucleophilic substitution reaction of an amine or an amide with an electrophilic reagent such as an acid halide, an acid anhydride, an alkyl halide, a halogen-substituted heterocyclic compound, etc. or a condensation reaction of an amine or an amide with an acid such as a carboxylic acid, etc. to prepare an amide, an imide or the like, which is then mixed with a base such as an alkali metal hydroxide, etc. or subjected to cation exchange.

The content of the basic compound (I) of the charge transfer material may be properly determined depending on the type of the charge transfer material. When the charge transfer material is a molten electrolytic salt composition described later, the content of the basic compound (I) is preferably $1\times10^{-7}$ to $1\times10^{-2}$ mol/g, more preferably $1\times10^{-6}$ to $1\times10^{-3}$ mol/g.

(B) Alkali Metal Salt and/or Alkaline Earth Metal Salt

The charge transfer material of the present invention preferably comprises an alkali metal salt and/or an alkaline earth metal salt together with the basic compound. Particularly, the charge transfer material preferably contains an alkali metal salt. The alkali metal salt is preferably a lithium salt or a sodium salt, more preferably a lithium salt. The alkaline earth metal salt is preferably a magnesium salt.

An anion coupled with an alkali metal cation or an alkaline earth metal cation to form a salt is not particularly limited. Examples of the anions include anions obtained from halide ions such as a fluoride ion, a chloride ion, a bromide ion and an iodide ion; a carboxylic acid; a sulfonic acid; a phosphonic acid; a sulfonamide; sulfonylimide such as a bis(trifluoromethane)sulfonimide and a bis(pentafluoroethane)sulfonimide; sulfonylmethide; sulfuric acid; thiocyanic acid; cyanic acid; perchloric acid; tetrafluoroboric acid; hexafluorophosphate; etc. The anion is preferably obtained from an iodide ion, a bis(trifluoromethane)sulfonimide, thiocyanic acid, a tetrafluoroboric acid or a hexafluorophosphate, particularly an anion obtaion from an iodide ion, a bis(trifluoromethane)sulfonimide or a tetrafluoroboric acid.

The total content of the alkali metal salt and/or the alkaline earth metal salt in the charge transfer material is properly determined depending on the type of the charge transfer material. When the charge transfer material is a molten electrolytic salt composition described below, the total content of the alkali metal salt and/or the alkaline earth metal salt is preferably $1\times10^{-8}$ to $1\times10^{-1}$ mol/g, more preferably $1\times10^{-7}$ to $1\times10^{-2}$ mol/g, particularly $1\times10^{-6}$ to $1\times10^{-3}$ mol/g.

When the charge transfer material of the present invention is a molten electrolytic salt composition described below, the molar ratio of the alkali metal salt and/or the alkaline earth metal salt to the basic compound in the charge transfer material is preferably 0.1 to 500, more preferably 0.5 to 100, particularly 1 to 20.

(C) Molten Salt Electrolyte

The charge transfer material of the present invention may be (i) an ion-conductive electrolytic composition or (ii) a carrier-conductive, charge-transporting material. Examples of the ion-conductive electrolytic compositions (i) include molten electrolytic salt compositions comprising molten electrolytic salts containing redox couples; electrolytic solutions is having redox couples dissolved in solvents; so-called gel electrolytic compositions having solutions containing redox couples penetrating into polymer matrices; solid electrolytic compositions; etc. Examples of the carrier-conductive, charge-transporting materials (ii) include electron-transporting materials and hole-transporting materials.

The charge transfer material of the present invention is preferably in a liquid state at the room temperature. When the charge transfer material of the present invention is a molten electrolytic salt composition, it is in a liquid state at room temperature, even when the above basic compound, the alkali metal salt, the alkaline earth metal salt, etc. are added. The basic compound is preferably in a molten state at room temperature. Namely, the basic compound is preferably a so-called room-temperature molten salt.

The charge transfer material of the present invention is preferably an ion-conductive electrolytic composition. The charge transfer material is preferably a molten electrolytic salt composition to satisfy both photoelectric conversion efficiency and durability. The molten electrolytic salt used in the molten electrolytic salt composition will be explained in detail below.

The molten salt is in a liquid state at room temperature or has a low melting point. Examples of the molten electrolytic salts include a pyridinium salt, an imidazolium salt and a triazolium salt disclosed in WO95/18456, JP 8-259543 A, "Denki Kagaku (Electrochemistry)," 65, 11, 923 (1997). The melting point of the molten electrolytic salt is preferably 100° C. or lower, particularly in a liquid state at around room temperature.

The molten salt electrolytes represented by the following general formulae (Y-a), (Y-b) and (Y-c) are preferably used in the present invention.

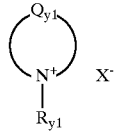 (Y-a)

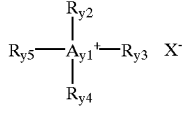 (Y-b)

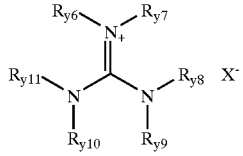 (Y-c)

In the general formula (Y-a), $Q_{y1}$ represents an atom group forming an aromatic cation having a 5- or 6-membered ring structure with a nitrogen atom. $Q_{y1}$ is preferably composed of atoms selected from the group consisting of carbon, hydrogen, nitrogen, oxygen and sulfur. The 5-membered ring formed by $Q_{y1}$ is preferably an oxazole ring, a thiazole ring, an imidazole ring, a pyrazole ring, an iso-oxazole ring, a thiadiazole ring, an oxadiazole ring, a triazole ring, an indole ring or a pyrrole ring, more preferably an oxazole ring, a thiazole ring or an imidazole ring, particularly an oxazole ring or an imidazole ring. The 6-membered ring formed by $Q_{y1}$ is preferably a pyridine ring, a pyrimidine ring, a pyridazine ring, a pyrazine ring or a triazine ring, more preferably a pyridine ring.

In the general formula (Y-b), $A_{y1}$ represents a nitrogen atom or a phosphorus atom.

$R_{y1}$ to $R_{y11}$ in the general formulae (Y-a), (Y-b) and (Y-c) independently represent substituted or unsubstituted alkyl groups preferably having 1 to 24 carbon atoms, which may be straight, branched or cyclic, such as a methyl group, an ethyl group, a propyl group, an isopropyl group, a pentyl group, a hexyl group, an octyl group, a 2-ethylhexyl group, a t-octyl group, a decyl group, a dodecyl group, a tetradecyl group, a 2-hexyldecyl group, an octadecyl group, a cyclohexyl group, a cyclopentyl group, etc.; or substituted or unsubstituted alkenyl groups preferably having 2 to 24 carbon atoms, which may be straight or branched, such as a vinyl group, an allyl group, etc. Each of $R_{y1}$ to $R_{y11}$ is more preferably an alkyl group having 2 to 18 carbon atoms or an alkenyl group having 2 to 18 carbon atoms, particularly an alkyl group having 2 to 6 carbon atoms.

Two or more of $R_{y2}$ to $R_{y5}$ in the general formula (Y-b) may be bonded together to form a non-aromatic ring containing $A_{y1}$. Two or more of $R_{y6}$ to $R_{y11}$ in the general formula (Y-c) may be bonded together to form a ring.

The general formulae (Y-a), (Y-b) and (Y-c) may have substituents. Preferable examples of the substituents include halogen atoms such as F, Cl, Br and I; a cyano group; alkoxy groups such as a methoxy group, an ethoxy group, a methoxyethoxy group and a methoxyethoxyethoxy group; aryloxy groups such as a phenoxy group; alkylthio groups such as a methylthio group and an ethylthio group; alkoxycarbonyl groups such as an ethoxycarbonyl group; carbonate groups such as an ethoxycarbonyloxy group; acyl groups such as an acetyl group, a propionyl group and a benzoyl group; sulfonyl groups such as a methanesulfonyl group and a benzenesulfonyl group; acyloxy groups such as an acetoxy group and a benzoyloxy group; sulfonyloxy groups such as a methanesulfonyloxy group and a toluenesulfonyloxy group; phosphonyl groups such as a diethylphosphonyl group; amido groups such as an acetylamino group and a benzoylamino group; carbamoyl groups such as an N,N-dimethylcarbamoyl group; alkyl groups such as a methyl group, an ethyl group, a propyl group, an isopropyl group, a cyclopropyl group, a butyl group, a 2-carboxyethyl group and a benzyl group; aryl groups such as a phenyl group and a toluyl group; heterocyclic groups such as a pyridyl group, an imidazolyl group and a furanyl group; alkenyl groups such as a vinyl group and a 1-propenyl group; silyl groups; silyloxy groups; etc.

The molten salt electrolytes represented by the general formula (Y-a), (Y-b) or (Y-c) may form oligomers or polymers via any one of $Q_{y1}$ and $R_{y1}$ to $R_{y11}$.

In the general formulae (Y-a), (Y-b) and (Y-c), $X^-$ represents an anion. Preferable examples of the anions include halide ions such as $I^-$, $Cl^-$ and $Br^-$, $SCN^-$, $BF_4^-$, $PF_6^-$, $ClO_4^-$, $N^-(SO_2CF_3)_2$, $N^-(SO_2CF_2CF_3)_2$, $CH_3SO_3^-$, $CF_3SO_3^-$, $CF_3COO^-$, $BPh_4^-$, $C^-(SO_2CF_3)_3$, etc. $X^-$ is more preferably $SCN^-$, $BF_4^-$, $N^-(SO_2CF_3)_2$, $CF_3SO_3^-$ or $CF_3COO^-$.

Preferred examples of the molten salt electrolytes are illustrated below without intention of restriction.

Y1 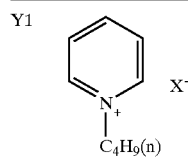

Y1-1: X⁻ = I⁻
Y1-2: X⁻ = BF₄⁻
Y1-3: X⁻ = N⁻(SO₂CF₃)₂
Y1-4: X⁻ = PF₆⁻

Y2 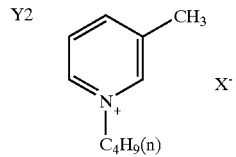

Y2-1: X⁻ = I⁻
Y2-2: X⁻ = BF₄⁻
Y2-3: X⁻ = N⁻(SO₂CF₃)₂
Y2-4: X⁻ = CF₃COO⁻
Y2-5: X⁻ = SCN⁻
Y2-6: X⁻ = CF₃SO₃⁻

Y3 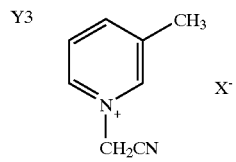

Y3-1: X⁻ = I⁻
Y3-2: X⁻ = BF₄⁻
Y3-3: X⁻ = N⁻(SO₂CF₃)₂

Y4 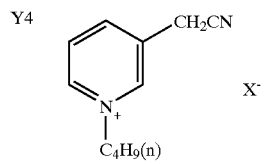

Y4-1: X⁻ = I⁻
Y4-2: X⁻ = BF₄⁻
Y4-3: X⁻ = N⁻(SO₂CF₃)₂

Y5 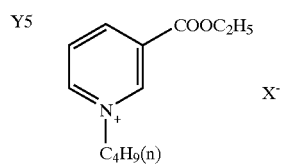

Y5-1: X⁻ = I⁻
Y5-2: X⁻ = BF₄⁻
Y5-3: X⁻ = N⁻(SO₂CF₃)₂

Y6 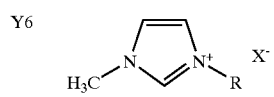

Y6-1: X⁻ = I⁻, R = Et
Y6-2: X⁻ = BF₄⁻, R = Et
Y6-3: X⁻ = N⁻(SO₂CF₃)₂, R = Et
Y6-4: X⁻ = Br⁻, R = Et
Y6-5: X⁻ = CF₃COO⁻, R = Et
Y6-6: X⁻ = SCN⁻, R = Et
Y6-7: X⁻ = CF₃SO₃⁻, R = Et

Y6-8: X⁻ = I⁻, R = ⁿPr
Y6-9: X⁻ = BF₄⁻, R = ⁿPr
Y6-10: X⁻ = N⁻(SO₂CF₃)₂, R = ⁿPr
Y6-11: X⁻ = I⁻, R = ⁿBu
Y6-12: X⁻ = BF₄⁻, R = ⁿBu
Y6-13: X⁻ = N⁻(SO₂CF₃)₂, R = ⁿBu

Y7 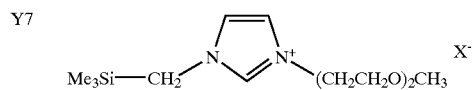

Y7-1: X⁻ = I⁻
Y7-2: X⁻ = BF₄⁻
Y7-3: X⁻ = N⁻(SO₂CF₃)₂
Y7-4: X⁻ = CF₃COO⁻
Y7-5: X⁻ = SCN⁻

Y8 

Y8-1: X⁻ = I⁻
Y8-2: X⁻ = BF₄⁻
Y8-3: X⁻ = N⁻(SO₂CF₃)₂
Y8-4: X⁻ = PF₆⁻
Y8-5: X⁻ = CF₃COO⁻
Y8-6: X⁻ = SCN⁻
Y8-7: X⁻ = CF₃SO₃⁻

Y9 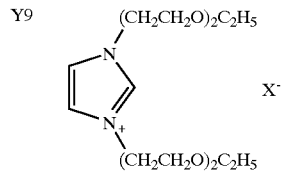

Y9-1: X⁻ = I⁻
Y9-2: X⁻ = BF₄⁻
Y9-3: X⁻ = N⁻(SO₂CF₃)₂
Y9-4: X⁻ = CF₃COO⁻
Y9-5: X⁻ = SCN⁻
Y9-6: X⁻ = CF₃SO₃⁻

-continued

| | | |
|---|---|---|
| Y10 | 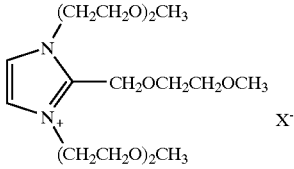 | Y10-1: X⁻ = I⁻<br>Y10-2: X⁻ = BF₄⁻<br>Y10-3: X⁻ = N⁻(SO₂CF₃)₂ |
| Y11 | 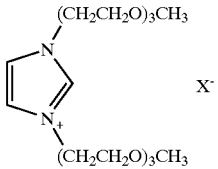 | Y11-1: X⁻ = I⁻<br>Y11-2: X⁻ = BF₄⁻<br>Y11-3: X⁻ = N⁻(SO₂CF₃)₂ |
| Y12 | 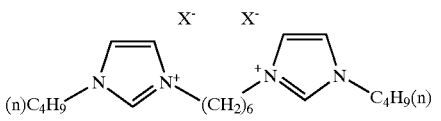 | Y12-1: X⁻ = I⁻<br>Y12-2: X⁻ = BF₄⁻<br>Y12-3: X⁻ = N⁻(SO₂CF₃)₂ |
| Y13 | 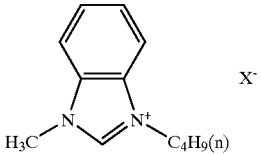 | Y13-1: X⁻ = I⁻<br>Y13-2: X⁻ = BF₄⁻<br>Y13-3: X⁻ = N⁻(SO₂CF₃)₂ |
| Y14 | 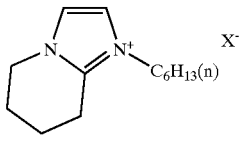 | Y14-1: X⁻ = I⁻<br>Y14-2: X⁻ = BF₄⁻<br>Y14-3: X⁻ = N⁻(SO₂CF₃)₂ |
| Y15 | 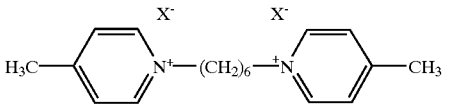 | Y15-1: X⁻ = I⁻<br>Y15-2: X⁻ = BF₄⁻<br>Y15-3: X⁻ = N⁻(SO₂CF₃)₂ |
| Y16 | 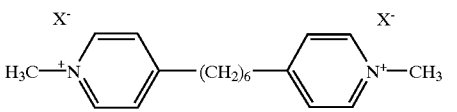 | Y16-1: X⁻ = I⁻<br>Y16-2: X⁻ = BF₄⁻<br>Y16-3: X⁻ = N⁻(SO₂CF₃)₂ |
| Y17 | 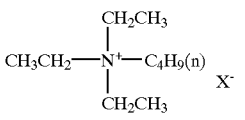 | Y17-1: X⁻ = I⁻<br>Y17-2: X⁻ = BF₄⁻<br>Y17-3: X⁻ = N⁻(SO₂CF₃)₂<br>Y17-4: X⁻ = PF₆⁻ |
| Y18 | 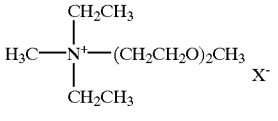 | Y18-1: X⁻ = I⁻<br>Y18-2: X⁻ = BF₄⁻<br>Y18-3: X⁻ = N⁻(SO₂CF₃)₂ |
| Y19 | 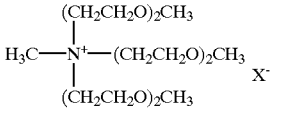 | Y19-1: X⁻ = I⁻<br>Y19-2: X⁻ = BF₄⁻<br>Y19-3: X⁻ = N⁻(SO₂CF₃)₂<br>Y19-4: X⁻ = CF₃COO⁻<br>Y19-5: X⁻ = SCN⁻<br>Y19-6: X⁻ = CF₃SO₃⁻ |
| Y20 | 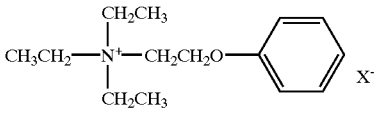 | Y20-1: X⁻ = I⁻<br>Y20-2: X⁻ = BF₄⁻<br>Y20-3: X⁻ = N⁻(SO₂CF₃)₂ |

-continued

| | | |
|---|---|---|
| Y21 | 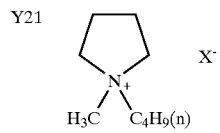 | Y21-1: X⁻ = I⁻<br>Y21-2: X⁻ = BF$_4^-$<br>Y21-3: X⁻ = N⁻(SO$_2$CF$_3$)$_2$ |
| Y22 | 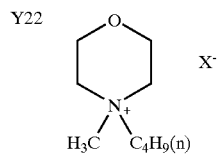 | Y22-1: X⁻ = I⁻<br>Y22-2: X⁻ = BF$_4^-$<br>Y22-3: X⁻ = N⁻(SO$_2$CF$_3$)$_2$ |
| Y23 | 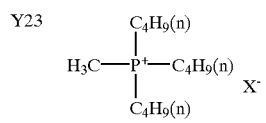 | Y23-1: X⁻ = I⁻<br>Y23-2: X⁻ = BF$_4^-$<br>Y23-3: X⁻ = N⁻(SO$_2$CF$_3$)$_2$ |
| Y24 | 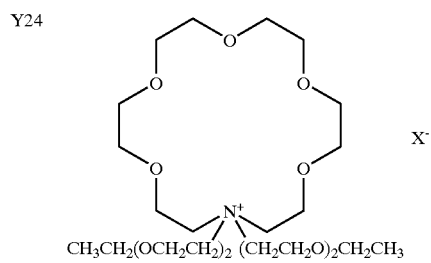 | Y24-1: X⁻ = I⁻<br>Y24-2: X⁻ = BF$_4^-$<br>Y24-3: X⁻ = N⁻(SO$_2$CF$_3$)$_2$ |
| Y25 | 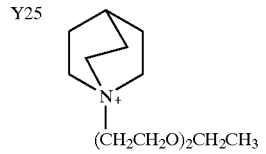 | Y25-1: X⁻ = I⁻<br>Y25-2: X⁻ = BF$_4^-$<br>Y25-3: X⁻ = N⁻(SO$_2$CF$_3$)$_2$ |
| Y26 | 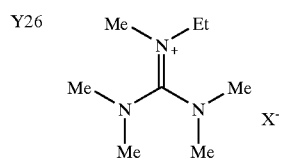 | Y26-1: X⁻ = I⁻<br>Y26-2: X⁻ = N⁻(SO$_2$CF$_3$)$_2$<br>Y26-3: X⁻ = BF$_4^-$<br>Y26-4: X⁻ = PF$_6^-$ |
| Y27 | 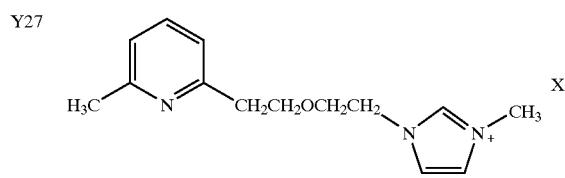 | Y27-1: X⁻ = I⁻<br>Y27-2: X⁻ = N⁻(SO$_2$CF$_3$)$_2$<br>Y27-3: X⁻ = BF$_4^-$<br>Y27-4: X⁻ = CF$_3$COO⁻<br>Y27-5: X⁻ = SCN⁻<br>Y27-6: X⁻ = CF$_3$SO$_3^-$ |
| Y28 | 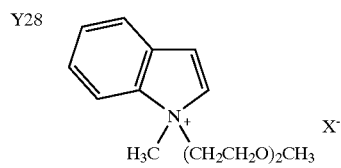 | Y28-1: X⁻ = I⁻<br>Y28-2: X⁻ = BF$_4^-$<br>Y28-3: X⁻ = N⁻(SO$_2$CF$_3$)$_2$ |
| Y29 | 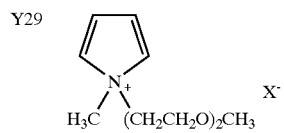 | Y29-1: X⁻ = I⁻<br>Y29-2: X⁻ = BF$_4^-$<br>Y29-3: X⁻ = N⁻(SO$_2$CF$_3$)$_2$ |

The molten salt electrolyte is preferably in a molten state at room temperature, and preferably does not need a solvent when used as a charge-transporting material. Though a solvent described below may be added, the content of the molten electrolytic salt is preferably 50% by mass or more, particularly 90% by mass or more, based on the entire charge transfer material.

(D) Gelation

The charge transfer material of the present invention may be gelled by adding a polymer or an oil-gelling agent, by the polymerization of monomers including a multifunctional monomer, by a cross-linking reaction of a polymer, etc.

In the case of adding a polymer to cause the gelation of the charge transfer material, usable polymers may be those described in "Polymer Electrolyte Reviews 1 and 2," edited by J. R. MacCallum and C. A. Vincent, ELSEIVER APPLIED SCIENCE. The preferable polymers are polyacrylonitrile and polyvinylidene fluoride.

In the case of adding an oil-gelling agent to cause the gelation of the charge transfer material, usable oil-gelling agents may be those described in J. Chem. Soc. Japan, Ind. Chem. Soc., 46, 779 (1943), J. Am. Chem. Soc., 111, 5542 (1989), J. Chem. Soc., Chem. Commun., 390 (1993), Angew. Chem. Int. Ed. Engl., 35, 1949 (1996), Chem. Lett., 885 (1996), J. Chem. Soc., Chem. Commun., 545 (1997), etc. The preferred oil-gelling agents have an amide structure. The amount of the oil-gelling agent used in the charge transfer material is generally 0.1 to 20% by mass, preferably 1 to 10% by mass, based on the entire charge transfer material. Further, the gelation method disclosed in JP 2000-58140 A may be used in the present invention.

In the case of the cross-linking reaction of a polymer to cause the gelation of the charge transfer material, it is preferable to use a polymer containing a group having cross-linking reactivity together with a cross-linking agent. The groups having cross-linking reactivity are preferably amino groups or nitrogen-containing heterocyclic groups, such as a pyridyl group, an imidazolyl group, a thiazolyl group, an oxazolyl group, a triazolyl group, a morpholyl group, a piperidyl group, a piperazyl group, etc. The cross-linking agent is preferably an electrophilic agent having a plurality of functional groups that may be attacked by a nitrogen atom, for example, multi-functional alkyl halides, aralkyl halides, sulfonates, acid anhydrides, acyl chlorides, isocyanates, $\alpha,\beta$-unsaturated sulfonyl compounds, $\alpha,\beta$-unsaturated carbonyl compounds, $\alpha,\beta$-unsaturated nitrile compounds, etc. The cross-linking methods disclosed in JP 2000-17076 A and JP 2000-86724 A may be used in the present invention.

(E) Iodine Salt and/or Iodine

The charge transfer material of the present invention preferably comprises an iodine salt and/or iodine. The iodine salt content is 50% by mass or more based on the entire salt in the charge transfer material. The iodine content is preferably 0.1 to 20% by mass, more preferably 0.5 to 5% by mass, based on the entire charge transfer material.

[2] Photoelectric Conversion Device

The photoelectric conversion device of the present invention has an electrically conductive layer, a layer of dye-adsorbed, fine semiconductor particles, a charge transfer layer and a counter electrode. The charge transfer layer comprises the above-mentioned charge transfer material of the present invention. The layer of dye-adsorbed, fine semiconductor particles is referred to hereinafter as a photosensitive layer.

As shown in FIG. 1, the photoelectric conversion device preferably has a laminate structure comprising an electrically conductive layer 10, an undercoating layer 60, a photosensitive layer 20 containing fine semiconductor particles 21 sensitized by dye 22 and an charge-transporting material 23 penetrating into voids among the fine semiconductor particles 21, a charge transfer layer 30, and a counter electrode layer 40 in this order. The charge-transporting material 23 in the photosensitive layer 20 may be generally the same as the charge transfer material of the present invention used in the charge transfer layer 30. The electrically conductive layer 10 and/or the counter electrode layer 40 may be supported by a substrate 50 to improve the strength of the photoelectric conversion device. A layer composed of the electrically conductive layer 10 and the substrate 50 optionally used for supporting it is referred to as "conductive support," and a layer composed of the counter electrode layer 40 and the substrate 50 optionally used for supporting it is referred to as "counter electrode" hereinafter. The electrically conductive layer 10, the counter electrode layer 40 and the substrate 50 shown in FIG. 1 may be transparent.

A photoelectric cell is constituted by connecting the photoelectric conversion device to an external circuit to electrically work or generate electricity in the external circuit. A photo sensor is such a photoelectric conversion device for sensing optical information. Such a photoelectric cell that has the charge transfer material mainly composed of an ion-conductive material is referred to as a photo-electrochemical cell. A photoelectric cell intended for power generation with solar light is referred to as a solar cell.

In the case of using n-type fine semiconductor particles in the photoelectric conversion device of the present invention shown in FIG. 1, a light introduced into the photosensitive layer 20 excites the dye 22, etc., to generate excited high-energy electrons, which are transported to a conduction band of the fine semiconductor particles 21, and are diffused to reach the electrically conductive layer 10. At this time, the dye 22 is in an oxidized form. In a photoelectric cell, electrons in the electrically conductive layer 10 return to the oxidized dye through the counter electrode layer 40 and the charge transfer layer 30 while doing job in an outside circuit, so that the dye 22 is regenerated. The photosensitive layer 20 generally acts as a negative electrode (photo-anode). The counter electrode layer 40 acts as a positive electrode. In a boundary of adjacent layers such as the electrically conductive layer 10 and the photosensitive layer 20; the photosensitive layer 20 and the charge transfer layer 30; the charge transfer layer 30 and the counter electrode layer 40; etc., components of each layer may be diffused and mixed. Each of the layers will be explained in detail below.

(A) Conductive Support

The conductive support is: (1) a single layer of the electrically conductive layer, or (2) two layers of the electrically conductive layer and the substrate. In the case (1), the electrically conductive layer is preferably made of a material having such a strength that it can fully seal the photoelectric conversion device, for example, a metal such as platinum, gold, silver, copper, zinc, titanium, aluminum and an alloy thereof. In the case (2), a substrate having the electrically conductive layer containing an electrically conductive material formed on the photosensitive layer side may be used. Preferable examples of the electrically conductive materials include metals such as platinum, gold, silver, copper, zinc, titanium, aluminum, indium and alloys thereof; carbon; electrically conductive metal oxides such as indium-tin composite oxides and tin oxides doped with fluorine or antimony; etc. The electrically conductive layer preferably has a thickness of 0.02 to 10 $\mu$m. The surface resistance of the conductive support is desirably as low as possible. The surface resistance of the conductive support is preferably 50 Ω/square or less, more preferably 20 Ω/square or less.

When light is irradiated from the conductive support side, it is preferred that the conductive support is substantially transparent. The term "substantially transparent" used herein means that 10% or more of light transmittance is obtained in part or all of a range from a visible light to a near infrared light (400 to 1200 nm). The light transmittance is preferably 50% or more, more preferably 80% or more. In particular, light transmittance is preferably high in a wavelength range where the photosensitive layer has sensitivity.

The transparent conductive support is preferably provided by forming the electrically conductive, transparent layer comprising an electrically conductive metal oxide on the transparent substrate of such material as a glass and a plastic by coating or vapor deposition. The electrically conductive, transparent layer is preferably made of tin dioxide doped with fluorine or antimony, or indium-tin oxide (ITO). The transparent substrate may be made of a glass such as a low-cost soda glass excellent in strength and a non-alkali glass suffering from no alkaline elution. In addition, a transparent polymer film may be used as the transparent substrate. Materials usable for the transparent polymer film are triacetylcellulose (TAC), polyethylene terephthalate (PET), polyethylene naphthalate (PEN), syndiotactic polystyrene (SPS), polyphenylenesulfide (PPS), polycarbonate (PC), polyarylate (PAr), polysulfone (PSF), polyestersulfone (PES), polyimide (PI), polyetherimide (PEI), cyclic polyolefin, brominated phenoxy resin, etc. To secure sufficient transparency, the amount of the electrically conductive metal oxide coated is preferably 0.01 to 100 g per 1 m$^2$ of the glass or plastic substrate.

It is preferable to use a metal lead to reduce the resistance of the transparent conductive support. The metal lead is preferably made of a metal such as platinum, gold, nickel, titanium, aluminum, copper, silver, etc. The metal lead is preferably formed on the transparent substrate by a vapor deposition method, a sputtering method, etc., preferably with a electrically conductive, transparent layer comprising conductive tin oxide or ITO formed thereon. Decrease in incident light quantity by the metal lead is suppressed to preferably 10% or less, more preferably 1 to 5%.

(B) Photosensitive Layer

The photosensitive layer comprises fine semiconductor particles sensitized by a dye. In the photosensitive layer, the fine semiconductor particles act as a photosensitive substance to absorb light and conduct charge separation, thereby generating electrons and positive holes. In the dye-sensitized, fine semiconductor particles, the light absorption and the generation of electrons and positive holes are primarily caused by the dye, and the fine semiconductor particles receive and convey electrons or positive holes. The semiconductor used in the present invention is preferably an n-type semiconductor, in which conductor electrons act as a carrier under a photo-excitation condition to generate anode current.

(1) Semiconductor

Used as the semiconductor may be simple semiconductor such as silicon and germanium; a III–V series compound semiconductor; a metal chalcogenide such as a metal oxide, a metal sulfide, a metal selenide and a composite thereof; a compound having a perovskite structure such as strontium titanate, calcium titanate, sodium titanate, barium titanate and potassium niobate; etc.

Preferable examples of the metal chalcogenide include oxides of titanium, tin, zinc, iron, tungsten, zirconium, hafnium, strontium, indium, cerium, yttrium, lanthanum, vanadium, niobium and tantalum; sulfides of cadmium, zinc, lead, silver, antimony and bismuth; selenides of cadmium or lead; cadmium telluride; etc. Additionally, compound semiconductors such as phosphides of zinc, gallium, indium or cadmium, selenides of gallium-arsenic or copper-indium, copper-indium sulfide, etc. may be used in the present invention. Further, composite semiconductors such as $M_xO_yS_z$ and $M_{1x}M_{2y}O$, are also preferably used in the present invention, wherein M, $M_1$ and $M_2$ independently represent a metal atom, O represents an oxygen atom, S represents a sulfur atom, and x, y and z represent numbers combined with each other to form a neutral molecule.

Specific examples of the semiconductor are preferably Si, $TiO_2$, $SnO_2$, $Fe_2O_3$, $WO_3$, ZnO, $Nb_2O_5$, CdS, ZnS, PbS, $Bi_2S_3$, CdSe, CdTe, $SrTiO_3$, GaP, InP, GaAs, $CuInS_2$ and $CuInSe_2$, more preferably $TiO_2$, ZnO, $SnO_2$, $Fe_2O_3$, $WO_3$, $Nb_2O_5$, CdS, PbS, CdSe, $SrTiO_3$, InP, GaAs, $CuInS_2$ and $CuInSe_2$, further preferably $TiO_2$ and $Nb_2O_5$, and particularly $TiO_2$. $TiO_2$ contains 70% by volume or more, particularly 100% by volume, of an anatase-type crystal structure. The semiconductor is preferably doped with a metal to increase electron conductivity thereof. This metal is preferably divalent or trivalent. Further, the semiconductor is preferably doped with a monovalent metal to prevent a reverse current from the semiconductor to the charge transfer layer.

The semiconductor used in the present invention may have a monocrystalline or polycrystalline structure. From the viewpoints of production cost, stable supply of raw materials, energy-payback time, etc., the semiconductor is preferably polycrystalline, particularly a porous layer of fine semiconductor particles. The photosensitive layer may partly contain an amorphous semiconductor.

The particle size of the fine semiconductor particles is generally on the level of nm to μm. The average size of primary semiconductor particles, which is determined by averaging the diameters of circles equivalent to projected areas thereof, is preferably 5 to 200 nm, more preferably 8 to 100 nm. Further, the average size of secondary semiconductor particles in dispersion is preferably 0.01 to 30 μm.

Two or more of the fine semiconductor particles having different particle size distributions may be used in combination for the photosensitive layer. In this case, the average particle size of the smaller particles is preferably 25 nm or less, more preferably 10 nm or less. To improve a light-capturing rate of the photoelectric conversion device by scattering ray of incident light, the fine semiconductor particles having a large particle size, e.g. approximately 100 to 300 nm in diameter, may be used for the photosensitive layer.

Two or more kinds of the fine semiconductor particles may be used in combination for the photosensitive layer. In this case, one is preferably $TiO_2$, ZnO, $Nb_2O_5$ or $SrTiO_3$ and the other is preferably $SnO_2$, $Fe_2O_3$ or $WO_3$. More preferred combinations are ZnO and $SnO_2$, ZnO and $WO_3$, ZnO and $SnO_2$ and $WO_3$, etc. When two or more fine semiconductor particles are combined, their particle sizes may differ. Particularly preferred is a combination of larger-diameter particles of $TiO_2$, ZnO, $Nb_2O_5$ or $SrTiO_3$ and smaller-diameter particles of $SnO_2$, $Fe_2O_3$ or $WO_3$. The larger-diameter particles are preferably 100 nm or more in an average size, while the smaller-diameter particles are preferably 15 nm or less in an average size.

Preferably usable to produce the fine semiconductor particles are sol-gel methods described in Sumio Sakka, "Science of Sol-Gel Method," issued by Agune Shofusha (1998), and "Thin Film-Coating Technology by Sol-Gel Method" (1995) issued by the Technical Information Association, etc.; and gel-sol methods described in Tadao Sugimoto, "Synthesis of Mono-Dispersion Particles and Control of Their Size and Form by Novel Gel-Sol Method," and MATERIA, Vol. 35, No. 9, pages 1012 to 1018 (1996). Also preferable is a method developed by Degussa, which comprises preparing oxides by subjecting chlorides to a high-temperature hydrolysis in an oxyhydrogen salt.

In the case of using the fine semiconductor particles of titanium oxide, the above-described sol-gel method, gel-sol method and high-temperature hydrolysis method are preferably used, and a sulfuric acid method and a chlorine method described in Manabu Seino, "Titanium oxide—Properties and Applied Technique," issued by Gihodo Shuppan, (1997) may also be used. Further preferable as the sol-gel method are those described in Christophe J. Barb'e, et al, the Journal of American Ceramic Society, Vol. 80, No. 12, pages 3157 to 3171 (1997) and Burnside, et al, Chemistry of Materials, Vol. 10, No. 9, pages 2419 to 2425.

(2) Layer of Fine Semiconductor Particles

The fine semiconductor particles may be applied to the conductive support by a method for coating a conductive support with a dispersion or colloidal solution containing fine semiconductor particles, in addition to the above-mentioned sol-gel method. A wet-type film production method is relatively advantageous for the mass production of the photoelectric conversion device, improvement of properties of the solution containing fine semiconductor particles, improvement of the adaptability of the conductive support, etc. Typical examples of such a wet-type film production method are a coating method, a printing method, an electrolytic deposition method and an electrodeposition method. Further, the layer of fine semiconductor particles may be formed by a metal oxidation method, an LPD method for precipitating a metal from a metal solution by ligand exchange, etc, a sputtering method, a vapor deposition method, a CVD method; or an SPD method for forming a metal oxide by a thermally decomposing, metal oxide precursor sprayed onto a heated substrate.

The dispersion containing fine semiconductor particles may be prepared by crushing the semiconductor in a mortar; by dispersing the semiconductor while grinding it in a mill, or by synthesizing and precipitating the fine semiconductor particles in a reaction solvent, etc. in addition to the above-mentioned sol-gel method.

Usable as dispersion solvents are water or organic solvents such as methanol, ethanol, isopropyl alcohol, citronellol, terpineol, dichloromethane, acetone, acetonitrile, ethyl acetate, etc. Polymers such as polyethylene glycol, hydroxyethylcellulose and carboxymethylcellulose, a surfactant, an acid, a chelating agent, etc. may be used as a dispersing agent, if necessary. Polyethylene glycol is preferably added to the dispersion, because changing the molecular weight of the polyethylene glycol makes it possible to control the viscosity of the dispersion and the porosity of the resultant layer of fine semiconductor particles, and form a layer of fine semiconductor particles resistant to peeling.

Preferable coating methods include application methods such as a roller method and a dipping method, metering methods such as an air-knife method and a blade method, etc. Further, preferable as methods for applying and metering in the same portion are a wire-bar method disclosed in JP 58-4589 B. a slide-hopper method described in U.S. Pat. Nos. 2,681,294, 2,761,419 and 2,761,791, an extrusion method, a curtain method, etc. Further preferable as commonly usable methods are a spin method and a spray method. Usable as wet printing methods are three major printing methods by relief printing, offset printing and gravure printing, as well as an intaglio printing method, a gum printing method, a screen printing method, etc. A film production method may be selected from these methods depending on the viscosity of the dispersion and the desired wet thickness.

The layer of fine semiconductor particles is not limited to a single layer. Dispersions comprising the fine semiconductor particles having different particle sizes may be coated to form a multi-layer. Alternatively, dispersions containing different fine semiconductor particles, binders or additives may be coated to form a multi-layer. The multi-layer coating is effective, when it is impossible to form a layer having a sufficient thickness by one coating step.

Generally, the thicker the layer of fine semiconductor particles (having an equal thickness to that of the photosensitive layer), the higher the light-capturing rate, because a larger amount of the dye is incorporated therein per a unit-projected area. In this case, however, there is large loss owing to recombination of electric charges because of increased diffusion distance of the generated electrons. Thus, the preferable thickness of the layer of fine semiconductor particles is 0.1 to 100 $\mu$m. In the photoelectric cell, the thickness of the layer of fine semiconductor particles is preferably 1 to 30 $\mu$m, more preferably 2 to 25 $\mu$m. The amount of the fine semiconductor particles applied to the substrate is preferably 0.5 to 100 g, more preferably 3 to 50 g, per 1 $m^2$ of the substrate.

After applying the fine semiconductor particles to the conductive support, the particles are preferably subjected to a heat treatment, thereby bringing them into electronic contact with each other, and increasing the strength of the resultant coating and the adherence to the support. The heating temperature is preferably 40 to 700° C., more preferably 100 to 600° C. High-temperature treatment is not preferable to a substrate having a low melting or softening point, such as a polymer film substrate, because it tends to deteriorate such a substrate. The heat treatment is preferably carried out at as low a temperature as possible, for example, 50 to 350° C., from the viewpoint of cost. Such a low-temperature heat treatment can be made possible by using a layer containing as fine semiconductor particles as 5 nm or less in average size, a mineral acid, a metal oxide precursor, etc. Further, the heat treatment may be carried out while applying an ultraviolet ray, an infrared ray, a microwave, an electric field, an ultrasonic wave, etc. to the fine semiconductor particles, to lower the heating temperature. To remove unnecessary organic compounds, etc., the heat treatment is preferably carried out in combination with evacuation, an oxygen plasma treatment, and washing with pure water, a solvent or a gas, etc.

After the heat treatment, the layer of fine semiconductor particles may be subjected to a chemical metal-plating using an aqueous titanium tetrachloride solution, etc. or electro-chemical metal-plating using an aqueous titanium trichloride solution, etc., to increase the surface area and purity of the fine semiconductor particles, thereby improving the efficiency of injecting electrons into the particles from the dye. Further, to prevent reverse current from the fine semiconductor particles to the charge transfer layer, it is effective that the fine semiconductor particles adsorb other low-electron conductivity organic compounds than the dye. The organic compound adsorbed preferably has a hydrophobic group.

The layer of fine semiconductor particles preferably has a large surface area to adsorb a large amount of dye. The layer of fine semiconductor particles coated onto the substrate has a surface area of preferably 10 times or more, more preferably 100 times or more, its projected area. The upper limit of the surface area is generally about 1000 times, though it is not particularly limited.

(3) Dye

Any compound capable of absorbing visible and near infrared rays to sensitize the semiconductor may be used as the dye for the photosensitive layer. Preferable examples of such dyes include metal complex dyes, methine dyes, porphyrin-type dyes and phthalocyanine dyes, and the metal complex dyes are particularly preferable. Two or more kinds of dyes may be used in combination to obtain a large photoelectric conversion wavelength region and high photoelectric conversion efficiency. In the case of using a plurality of dyes, the kinds and mixing ratios of the dyes may be determined depending on the wavelength region and strength distribution of the light source.

The dye preferably has an appropriate interlocking group for interacting with the surface of the fine semiconductor particles. Preferable interlocking groups include acidic groups such as —COOH, —OH, —SO$_2$H, —P(O)(OH)$_2$ and —OP(O)(OH)$_2$ and π-conductive chelating groups such as oxime, dioxime, hydroxyquinoline, salicylate and α-ketoenolate groups. Particularly preferable among them are —COOH, —P(O)(OH)$_2$ and —OP(O)(OH)$_2$. The interlocking group may form a salt with an alkali metal, etc. or an intramolecular salt. If the methine chain of the polymethine dye has an acidic group as in the case where the methine chain forms a squarylium or croconium ring, it may act as the interlocking group.

The preferred dyes used for the photosensitive layer are specifically described below.

(a) Metal Complex Dye

When the dye is a metal complex dye, the dye is preferably a metallophthalocyanine dye, a metalloporphyrin dye or a ruthenium complex dye, and it is particularly a ruthenium complex dye. The ruthenium complex dyes described in U.S. Pat. Nos. 4,927,721, 4,684,537, 5,084,365, 5,350,644, 5,463,057 and 5,525,440, JP 7-249790 A, JP 10-504512 A and JP 2000-26487A, WO 98/50393, etc. may be used in the present invention.

The ruthenium complex dye is preferably represented by the following formula (III):

$$(A_3)_p Ru(B\text{-}a)(B\text{-}b)(B\text{-}c) \quad (III),$$

wherein A$_3$ represents a unidentate or bidentate ligand, preferably selected from the group consisting of Cl, SCN, H$_2$O, Br, I, CN, NCO, SeCN, a β-diketone derivative, an oxalate derivative and a dithiocarbamate derivative; p is an integer of 0 to 3; and B-a, B-b and B-c are independently organic ligands represented by the following formulae B-1 to B-10.

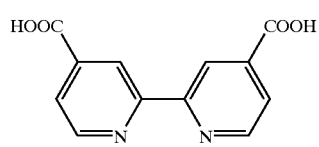

B-1

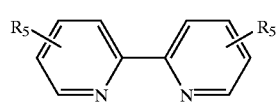

B-2

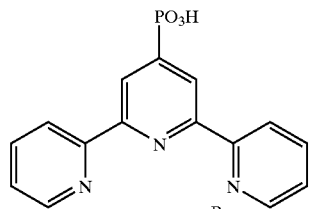

B-3

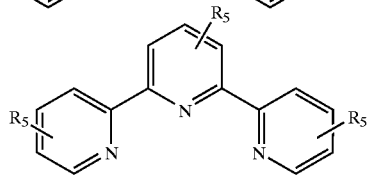

B-4

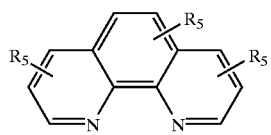

B-5

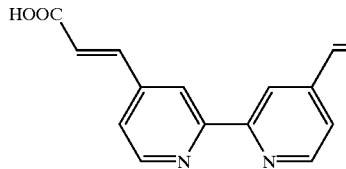

B-6

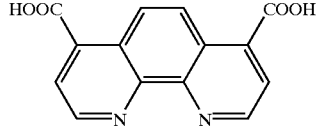

B-7

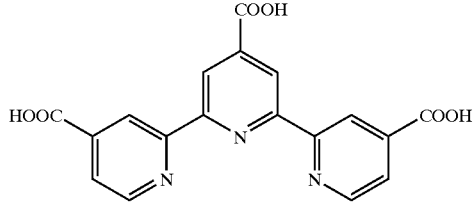

B-8

B-9

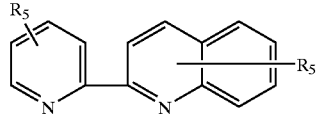

B-10

In the formulae B-1 to B-10, R$_5$ represents a hydrogen atom or a substituent. Specific examples of such substituents include a halogen atom, a substituted or unsubstituted alkyl group having 1 to 12 carbon atoms, a substituted or unsubstituted aralkyl group having 7 to 12 carbon atoms, a substituted or unsubstituted aryl group having 6 to 12 carbon atoms, the above-mentioned acidic group that may form a salt and a chelating group, etc. The alkyl group and the alkyl moiety of the aralkyl group may be straight or branched, and the aryl group and an aryl moiety of the aralkyl group may have a monocyclic or a polycyclic structure such as a condensed ring and a ring assembly. B-a, B-b and B-c may be the same or different, and one or two of them may exist.

Preferred examples of the metal complex dyes are illustrated below without intention of restriction.

| R | $A_3$ | p | B-a | B-b | B-c | $R_5$ |
|---|---|---|---|---|---|---|
| | | | $(A_3)_p Ru(B-a)(B-b)(B-c) \ldots$ (III), | | | |
| R-1 | SCN | 2 | B-1 | B-1 | — | — |
| R-2 | CN | 2 | B-1 | B-1 | — | — |
| R-3 | Cl | 2 | B-1 | B-1 | — | — |
| R-4 | CN | 2 | B-7 | B-7 | — | — |
| R-5 | SCN | 2 | B-7 | B-7 | — | — |
| R-6 | SCN | 2 | B-1 | B-2 | — | H |
| R-7 | SCN | 1 | B-1 | B-3 | — | — |
| R-8 | Cl | 1 | B-1 | B-4 | — | H |
| R-9 | I | 2 | B-1 | B-5 | — | H |
| R-10 | SCN | 3 | B-8 | — | — | — |
| R-11 | CN | 3 | B-8 | — | — | — |
| R-12 | SCN | 1 | B-2 | B-8 | — | H |
| R-13 | — | 0 | B-1 | B-1 | B-1 | — |
R14
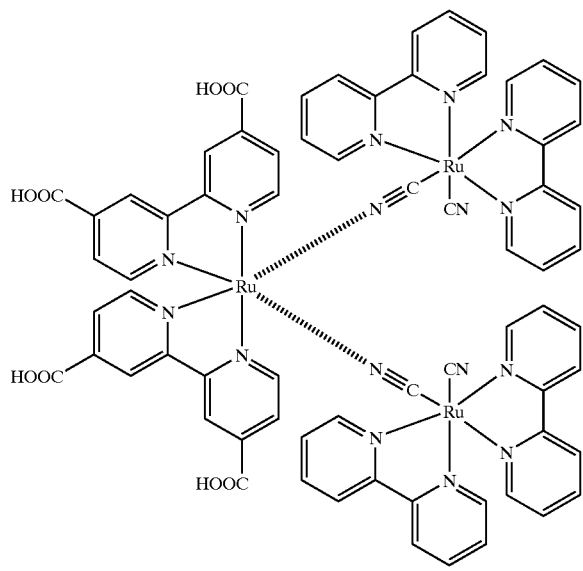
R15
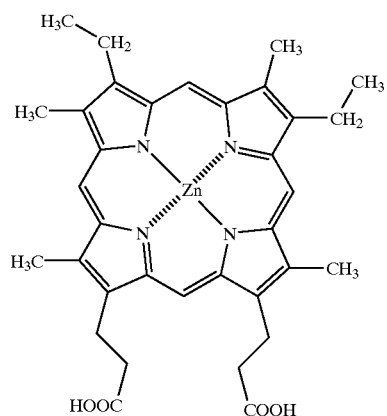

| -continued |
|---|
| $(A_3)_p Ru(B\text{-}a)(B\text{-}b)(B\text{-}c) \ldots$ (III), |

| R | $A_3$ | p | B-a | B-b | B-c | $R_5$ |
|---|---|---|---|---|---|---|
| R16 | | | | | | |
| R17 | | | | | | |

(b) Methine Dye

The methine dyes used in the present invention are preferably cyanine dyes, merocyanine dyes or polymethine dyes such as a squarylium dyes. Preferable examples of the polymethine dyes usable in the present invention are described in JP 11-35836 A, JP 11-67285 A, JP 11-86916 A, JP 11-97725 A, JP 11-158395 A, JP 11-163378 A, JP 11-214730 A, JP 11-214731 A, JP 11-238905 A and JP 2000-26487 A, European Patents 892411, 911841 and 991092. The preferred methine dyes are specifically described below.

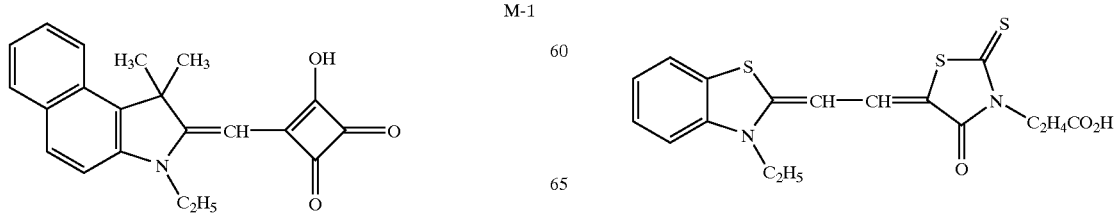

-continued

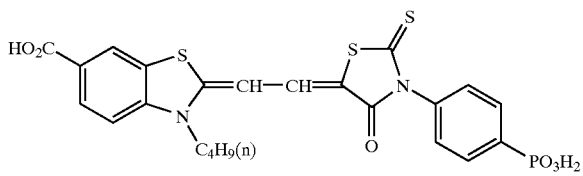
M-4

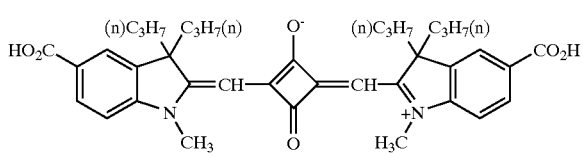
M-5

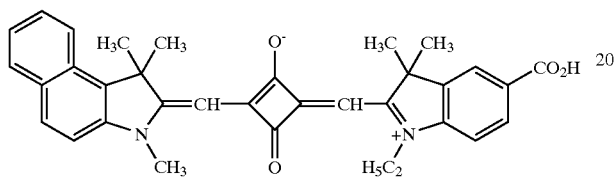
M-6

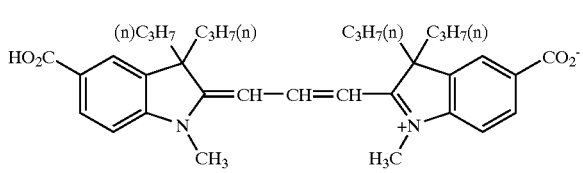
M-7

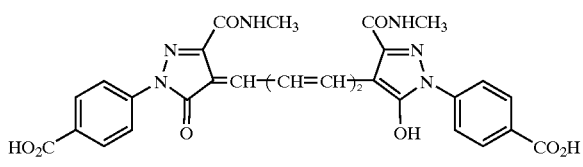
M-8

(4) Adsorption of Dye onto Fine Semiconductor Particles

The dye may be adsorbed onto the fine semiconductor particles by soaking the conductive support having the well-dried layer of fine semiconductor particles in a dye solution, or by coating the dye solution to the layer of fine semiconductor particles. In the former case, a soaking method, a dipping method, a roller method, an air-knife method, etc. may be used. In the soaking method, the dye may be adsorbed at a room temperature or under reflux while heating as described in JP 7-249790 A. As a coating method of the latter, a wire-bar method, a slide-hopper method, an extrusion method, a curtain method, a spin-coating method, a spraying method, etc. may be used. Also, pigment may be applied in the form of image to the substrate by an inkjet method, etc., and this image per se may be used as a photoelectric conversion device.

Preferable examples of solvents for dissolving the dye include alcohols such as methanol, ethanol, t-butanol and benzyl alcohol; nitrites such as acetonitrile, propionitrile and 3-methoxypropionitrile; nitromethane; halogenated hydrocarbons such as dichloromethane, dichloroethane, chloroform and chlorobenzene; ethers such as diethylether and tetrahydrofuran; dimethylsulfoxide; amides such as N,N-dimethylformamide and N,N-dimethylacetamide; N-methylpyrrolidone; 1,3-dimethylimidazolidinone; 3-methyloxazolidinone; esters such as ethyl acetate and butyl acetate; carbonates such as diethyl carbonate, ethylene carbonate and propylene carbonate; ketones such as acetone, 2-butanone and cyclohexanone; hydrocarbons such as hexane, petroleum ether, benzene and toluene; and mixtures thereof.

To weaken interaction such as association between the dyes and/or to increase the amount of adsorption of the dye onto the fine semiconductor particles, a colorless compound may be co-adsorbed onto the fine semiconductor particles together with the dye. Preferable examples of the colorless compound include steroid compounds having a carboxyl group such as chenodeoxycholic acid; sulfonic acid compounds; sulfonates; ureide compounds; alkali metal salts; alkaline earth metal salts; etc. Preferable among them are ureide compounds, alkali metal salts and alkaline earth metal salts, and particularly preferable are alkali metal salts.

The preferable sulfonate used as the colorless compound will be specifically described below.

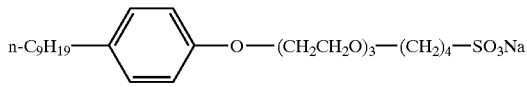
(W-1)

The preferred ureide compounds usable as the colorless compounds are specifically described below. The amount of the ureide compound in the dye solution is preferably 0.1 to 1000 mole equivalent, more preferably 1 to 500 mole equivalent, particularly 10 to 100 mole equivalent, to the dye.

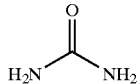
(D-1)

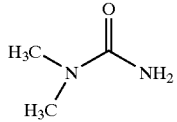
(D-2)

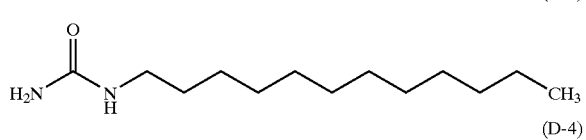
(D-3)

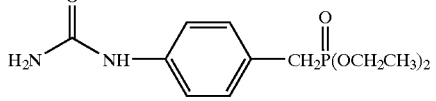
(D-4)

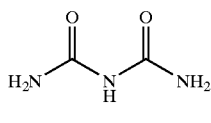
(D-5)

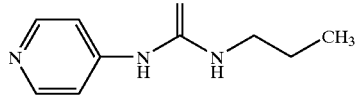
(D-6)

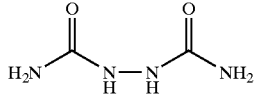
(D-7)

-continued

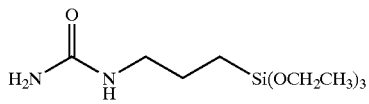
(D-8)

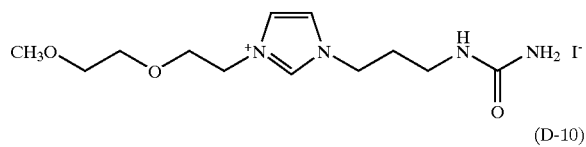
(D-9)

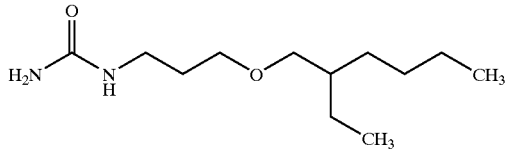
(D-10)

The alkali metal salt used as the colorless compound is preferably a lithium salt. An anion coupled with a lithium cation to form a salt is not particularly limited. Preferred examples of the anions include anions obtained from halide ions such as a fluoride ion, a chloride ion, a bromide ion and an iodide ion; carboxylic acids; sulfonic acids; phosphonic acids; a sulfonamides; sulfonylimides such as bis(trifluoromethane)sulfonimide and bis(pentafluoroethane) sulfonimide; sulfonylmethides; sulfuric acid; thiocyanic acids; cyanic acid; perchloric acids; tetrafluoroboric acids; or hexafluorophosphate. A further preferred anion is obtained from an iodide ion, bis(trifluoromethane) sulfonimide, a thiocyanic acid, a tetrafluoroboric acid or hexafluorophosphate; a particularly preferred anion is obtained from an iodide ion, bis(trifluoromethane) sulfonimide or a tetrafluoroboric acid; and the most preferred anion is obtained from an iodide ion.

The amount of the alkali metal salt or the alkaline earth metal salt in the dye adsorption solution is preferably 0.1 to 1000 mole equivalent, more preferably 1 to 500 mole equivalent, particularly 10 to 100 mole equivalent, to the dye.

The dye not adsorbed on the layer of fine semiconductor particles is preferably removed by washing immediately after the dye adsorption process. The washing is preferably carried out by a wet-type washing bath with a polar solvent such as acetonitrile or an organic solvent such as alcohol.

The total amount of the dye adsorbed is preferably 0.01 to 100 mmol per a unit surface area (1 m$^2$) of the layer of fine semiconductor particles. The amount of the dye adsorbed onto the fine semiconductor particles is preferably 0.01 to 1 mmol per 1 g of the fine semiconductor particles. With this adsorption amount of the dye, the semiconductor can be sufficiently sensitized. Too small an amount of the dye results in insufficient sensitization. On the other hand, if the amount of the dye is excessive, the dye not adsorbed onto the fine semiconductor particles is free, thereby reducing the sensitization of the fine semiconductor particles. To increase the adsorption amount of the dye, it is preferable that the layer of fine semiconductor particles is subjected to a heat treatment before the dye is adsorbed thereonto. After the heat treatment, it is preferable for the layer of fine semiconductor particles to quickly adsorb the dye while it is still at 60 to 150° C. without returning to the room temperature, to prevent water from adsorbing onto the layer of fine semiconductor particles.

(5) Treatment of Fine Semiconductor Particles

After the adsorption of the dye onto the fine semiconductor particles, it is preferable that the fine semiconductor particles are subjected to a treatment by a proper treatment compound. The term "treatment" used herein means an operation of bringing the fine semiconductor particles into contact with the treatment compound for a certain period of time. The term "in contact for a certain period of time" used herein means that at least one molecule of the treatment compound impinges on atoms on the fine semiconductor particles at least once for 0.1 second or more, preferably 1 second to 72 hours, more preferably 10 seconds to 24 hours.

Preferred examples of the treatment compound include ureide compounds, thiouredide compounds and silyl compounds. The treatment compound is more preferably a ureide compound, particularly a ureide compound having at least one silyl substituent group, which can be adsorbed onto the fine semiconductor particles after treatment. Specific examples of the ureide compounds, the thiouredide compounds and silyl compounds usable as the treatment compound will be illustrated below without intention of restriction.

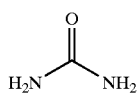
(A-1)

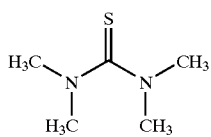
(A-2)

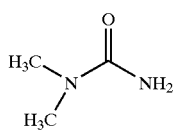
(A-3)

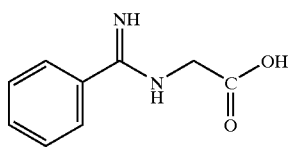
(A-4)

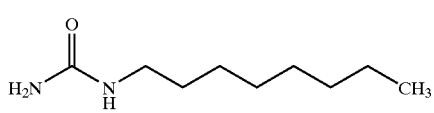
(A-5)

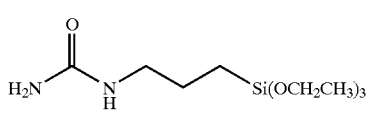
(A-6)

-continued
(A-7) 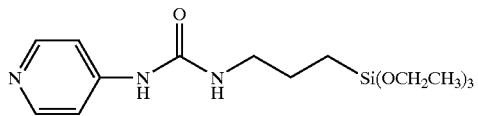
(A-8) 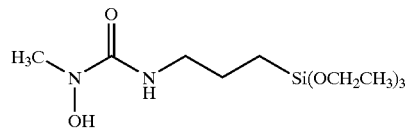
(A-9) 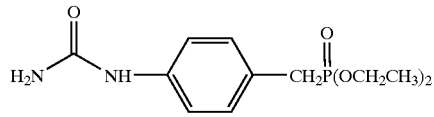
(A-10) 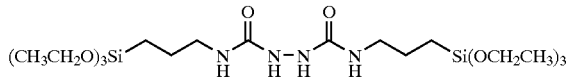
(A-11) 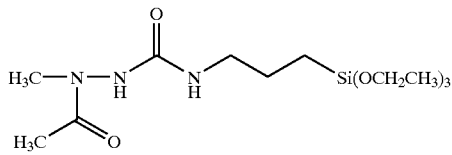
(A-12) 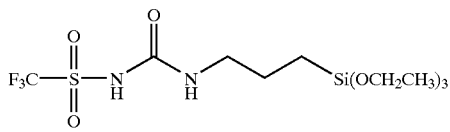
(A-13) 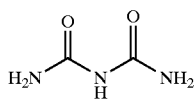
(A-14) 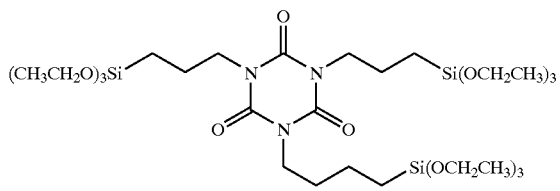
(A-15) 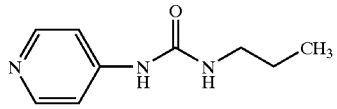
(A-16) 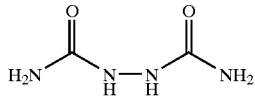
(A-17) 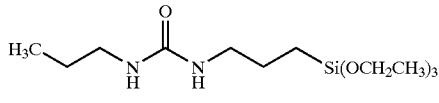
(A-18) 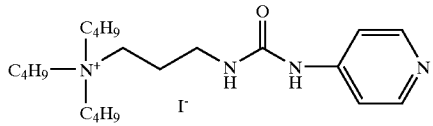
(A-19) 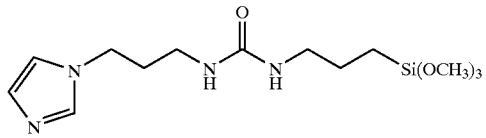
(A-20) 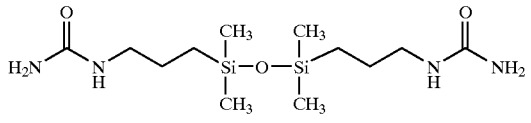
(A-21) 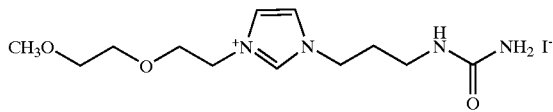
(A-22) Si(OCH$_2$CH$_3$)$_4$ (A-23)
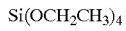
(A-24) 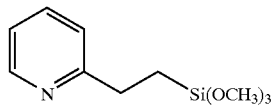
(A-25) 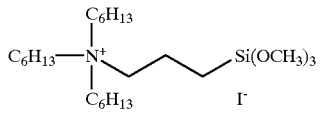

-continued

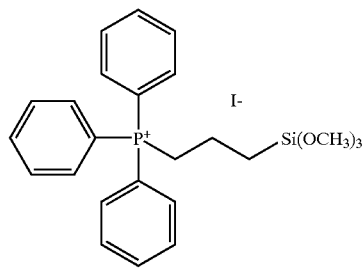
(A-26)

n-C$_8$H$_{17}$Si(OCH$_2$CH$_3$)$_3$ (A-27)

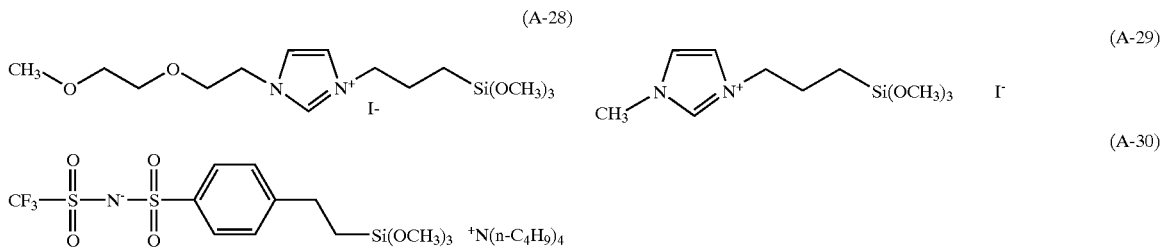

(A-28) (A-29)

(A-30)

The treatment compound is preferably used, dissolved or dispersed in a solvent, more preferably dissolved in a solvent. When the treatment compound per se is liquid, it may be used without a solvent. The treatment compound dissolved or dispersed in a solvent is referred to hereinafter as a treating liquid.

A solvent for the treating liquid is preferably an organic solvent. The organic solvent may be selected depending on the solubility of the treatment compound. Examples of the organic solvents include alcohols such as methanol, ethanol, t-butanol and benzyl alcohol; nitrites such as acetonitrile, propionitrile and 3-methoxypropionitrile; nitromethane; halogenated hydrocarbons such as dichloromethane, dichloroethane, chloroform and chlorobenzene; ethers such as diethylether and tetrahydrofuran; dimethylsulfoxide; amides such as N,N-dimethylformamide and N,N-dimethylacetamide; N-methylpyrrolidone; 1,3-dimethylimidazolidinone; 3-methyloxazolidinone; esters such as ethyl acetate and butyl acetate; carbonates such as diethyl carbonate, ethylene carbonate and propylene carbonate; ketones such as acetone, 2-butanone and cyclohexanone; hydrocarbons such as hexane, petroleum ether, benzene and toluene; and mixtures thereof. Preferable among them are nitrites, alcohols and amides.

A treatment method using the treating liquid is preferably a method for immersing the layer of fine semiconductor particles in the treating liquid (hereinafter referred to as "immersion treatment method"). A method for spraying the treating liquid onto the layer of fine semiconductor particles for a predetermined period of time may also be used. In carrying out the immersion treatment method, the temperature and immersion time of the treating liquid may be set arbitrarily, though immersion at a temperature of 20 to 80° C. for 30 seconds to 24 hours is preferable. After the immersion, the layer of fine semiconductor particles is preferably washed with a solvent. The solvent used for washing may be the same as used for the treating liquid, or polar solvents such as nitrites, alcohols, amides, etc.

Added to the above treating liquid is preferably amines or quaternary salts, particularly amines. Examples of amines added are preferably pyridines such as pyridine, 4-t-butylpyridine, 4-methoxypyridine, polyvinylpyridine, etc., more preferably 4-t-butylpyridine and 4-methoxypyridine. The quaternary salts added are preferably tetrabutylammonium iodide, tetrahexylammonium iodide, etc.

(C) Charge Transfer Layer

The charge transfer layer supplies electrons to the oxidized dye. The charge transfer layer comprises the charge transfer material of the present invention mentioned above. The charge transfer layer may comprise a plurality of the charge transfer materials.

The charge transfer layer may be formed by any of the following two methods. One method is to attach a counter electrode to a photosensitive layer beforehand and cause a charge transfer material in a liquid state to penetrate into a gap therebetween. Another method is to directly form a charge transfer layer on a photosensitive layer, and then form a counter electrode thereon.

In the former method, the charge transfer material may be caused to penetrate into the gap by a normal pressure process utilizing capillarity, or by a reduced pressure process where the material is sucked into the gap to replace a gas phase therein with a liquid phase.

In the case of forming a wet charge transfer material by the latter method, the wet charge transfer material is applied to the photosensitive layer, the counter electrode is disposed on the wet charge transfer material without drying it, and edges thereof are treated to prevent liquid leakage, if necessary. In the case of providing a gel charge transfer layer by the latter method, the charge transfer material may be applied in a liquid state and gelled by polymerization, etc. In this case, a counter electrode may be attached to the charge transfer layer after drying and fixing the charge transfer layer. The application of the electrolytic solution, the wet organic hole-transporting material, the gel electrolytic composition, etc. may be carried out by the same method as in the above-mentioned application of fine semiconductor particles and dyes.

In the case of a solid electrolytic composition and a solid hole transporting material, the charge transfer layer may be formed by a dry film-forming method such as a vacuum deposition method and a CVD method, followed by attaching a counter electrode thereto. The organic hole-transporting material may be introduced into the photosensitive layer by a vacuum deposition method, a casting method, a coating method, a spin-coating method, a soaking method, an electrolytic polymerization method, a photopolymerization method, etc. The inorganic hole-transporting material may be introduced into the photosensitive layer by a casting method, a coating method, a spin-coating method, a soaking method, an electrolytic deposition method, an electroless deposition method, etc.

(D) Counter Electrode

Like the above conductive support, the counter electrode may be an electrically conductive layer alone or a laminate of the electrically conductive layer and the substrate. Examples of electrically conductive materials used for the counter electrode layer include metals such as platinum, gold, silver, copper, aluminum, magnesium and indium; carbon; and electrically conductive metal oxides such as an indium-tin composite oxide and a fluorine-doped tin oxide. Preferable among them are platinum, gold, silver, copper, aluminum and magnesium. The substrate for the counter electrode is preferably a glass or a plastic plate, to which the above electrically conductive material is appied by coating or vapor deposition. The counter electrode layer preferably has a thickness of 3 nm to 10 µm, although the thickness is not particularly limited. The surface resistance of the counter electrode layer is desirably as low as possible. The surface resistance is preferably 50 Ω/square or less, more preferably 20 Ω/square or less.

Because light may be irradiated from either one or both sides of the conductive support and the counter electrode, at least one of them should be substantially transparent so that light can reach the photosensitive layer. To improve the efficiency of power generation, it is preferable that the conductive support is substantially transparent to permit light to pass therethrough. In this case, the counter electrode is preferably reflective to light. Such a counter electrode may be a glass or a plastic plate vapor-deposited with a metal or an electrically conductive oxide, or a thin metal film.

The counter electrode may be formed by coating, plating or vapor deposition (PVD, CVD, etc.) of the electrically conductive material directly onto the charge transfer layer, or by attaching the electrically conductive layer formed on the substrate to the charge transfer layer. Like in the conductive support, it is preferable to use a metal lead to reduce the resistance of the counter electrode, particularly when the counter electrode is transparent. Preferable materials and formation methods of the metal lead, decrease in the amount of incident light, etc. are the same as in the conductive support.

(E) Other Layers

A thin, dense semiconductor film is preferably formed as an undercoating layer between the conductive support and the photosensitive layer, to prevent short-circuiting between the counter electrode and the conductive support. The prevention of short-circuiting by this undercoating layer is effective particularly in the case of the charge transfer layer comprising the electron-transporting material or the hole-transporting material. The undercoating layer is made of preferably $TiO_2$, $SnO_2$, $Fe_2O_3$, $WO_3$, ZnO or $Nb_2O_5$, more preferably $TiO_2$. The undercoating layer may be formed by a spray-pyrolysis method described in Electrochim. Acta, 40, 643 to 652 (1995), a sputtering method, etc. The thickness of the undercoating layer is preferably 5 to 1000 nm, more preferably 10 to 500 nm.

Functional layers such as a protective layer and a reflection-preventing layer may be formed on either one or both of the conductive support and the counter electrode acting as electrodes, between the electrically conductive layer and the substrate, or in the substrate. The functional layers may be formed by a coating method, a vapor deposition method, an attaching method, etc. depending on their materials.

(F) Interior Structure of Photoelectric Conversion Device

As described above, the photoelectric conversion device may have various interior structures depending on its use. It is classified into two major structures, one allowing light incidence from both faces, and another allowing it from only one side. FIGS. 2 to 9 illustrate the interior structures of the photoelectric conversion device, to which the present invention is preferably applicable.

Figure 2:
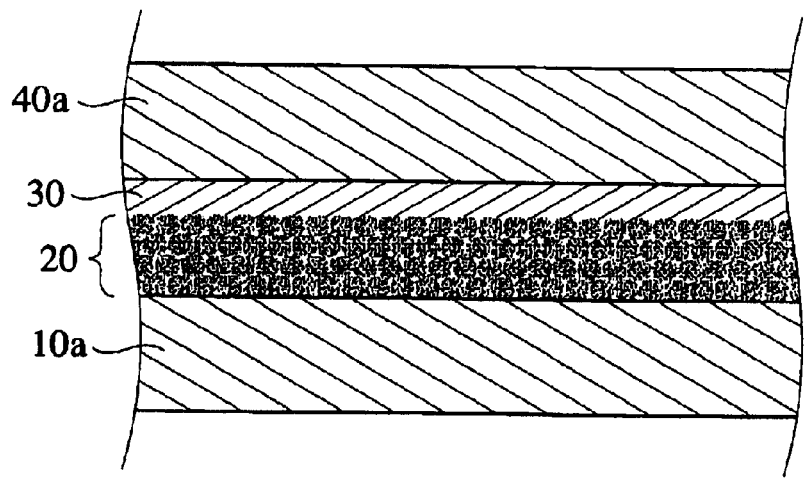
FIG. 2 is a partial cross sectional view showing another preferable structure of the photoelectric conversion device of the present invention.

In the structure illustrated in FIG. 2, a photosensitive layer 20 and a charge transfer layer 30 are formed between an electrically conductive, transparent layer 10a and a transparent counter electrode layer 40a. This structure allows light incidence from both sides of the device.

Figure 3:
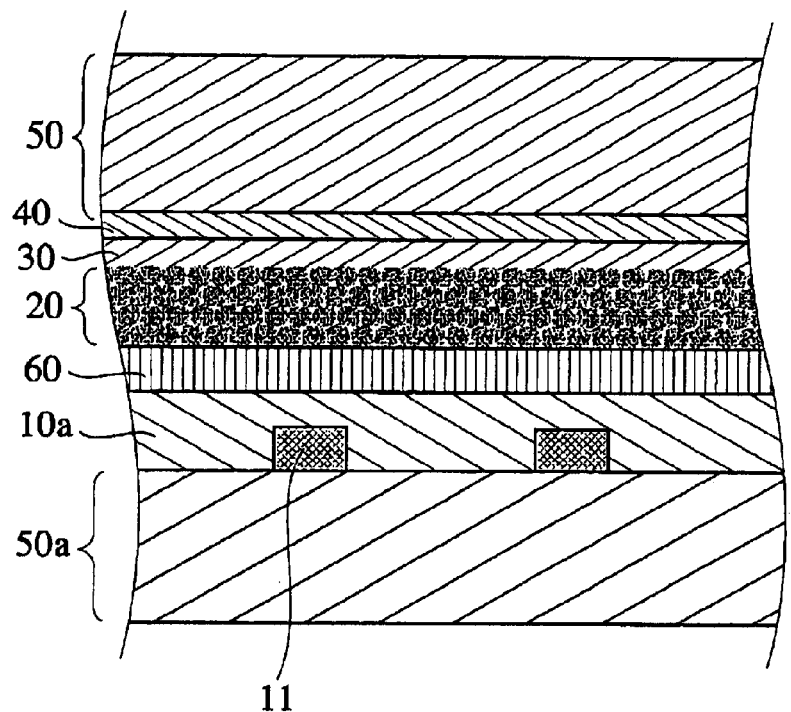
FIG. 3 is a partial cross sectional view showing a further preferable structure of the photoelectric conversion device of the present invention.

In the structure illustrated in FIG. 3, a transparent substrate 50a partially having a metal lead 11 is provided with an electrically conductive, transparent layer 10a, an undercoating layer 60, a photosensitive layer 20, a charge transfer layer 30 and a counter electrode layer 40 in this order, and further provided with a substrate 50 thereon. This structure allows light incidence from the side of the electrically conductive layer.

Figure 4:
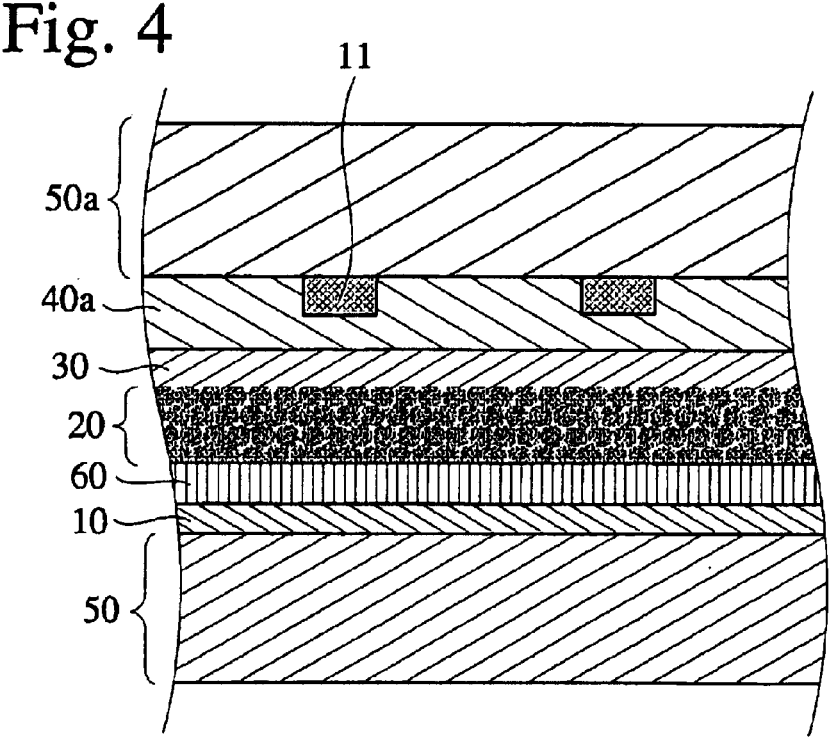
FIG. 4 is a partial cross sectional view showing a still further preferable structure of the photoelectric conversion device of the present invention.

In the structure illustrated in FIG. 4, a substrate 50 having an electrically conductive layer 10 is provided with a photosensitive layer 20 via an undercoating layer 60, and then provided with a charge transfer layer 30 and a transparent counter electrode layer 40a thereon, and further provided with a transparent substrate 50a locally having a metal lead 11 inside. This structure allows light incidence from the side of the counter electrode.

Figure 5:
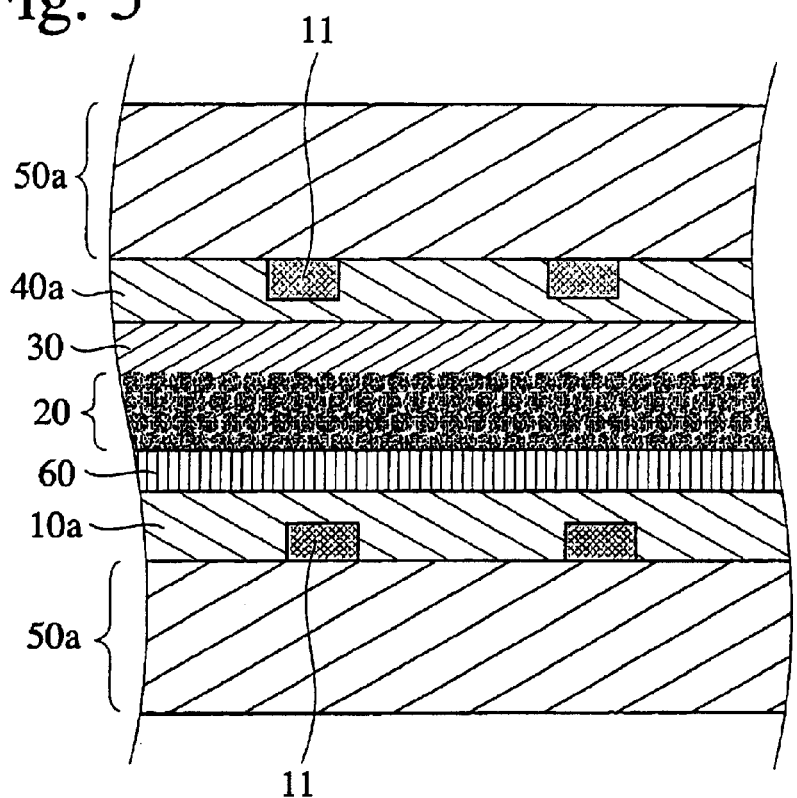
FIG. 5 is a partial cross sectional view showing a still further preferable structure of the photoelectric conversion device of the present invention.

In the structure illustrated in FIG. 5, two transparent substrates 50a each partially having a metal lead 11 are provided with an electrically conductive transparent layer 10a or 40a, and then provided with an undercoating layer 60, a photosensitive layer 20 and a charge transfer layer 30 between the conductive layers. This structure allows light incidence from both sides of the photoelectric conversion device.

Figure 6:
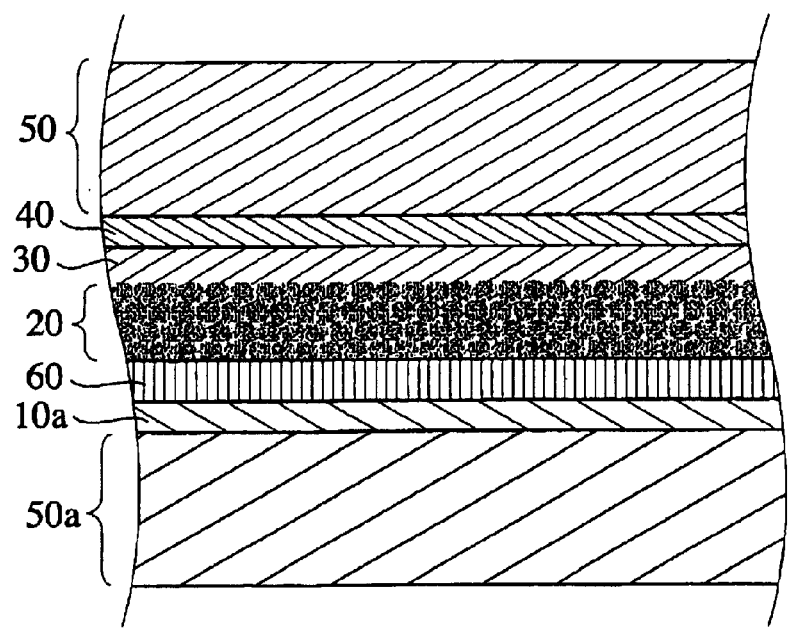
FIG. 6 is a partial cross sectional view showing a still further preferable structure of the photoelectric conversion device of the present invention.

In the structure illustrated in FIG. 6, a transparent substrate 50a is provided with an electrically conductive transparent layer 10a, an undercoating layer 60, a photosensitive layer 20, a charge transfer layer 30 and a counter electrode layer 40 in this order, and then attached to a substrate 50. This structure allows light incidence from the side of the electrically conductive layer.

Figure 7:
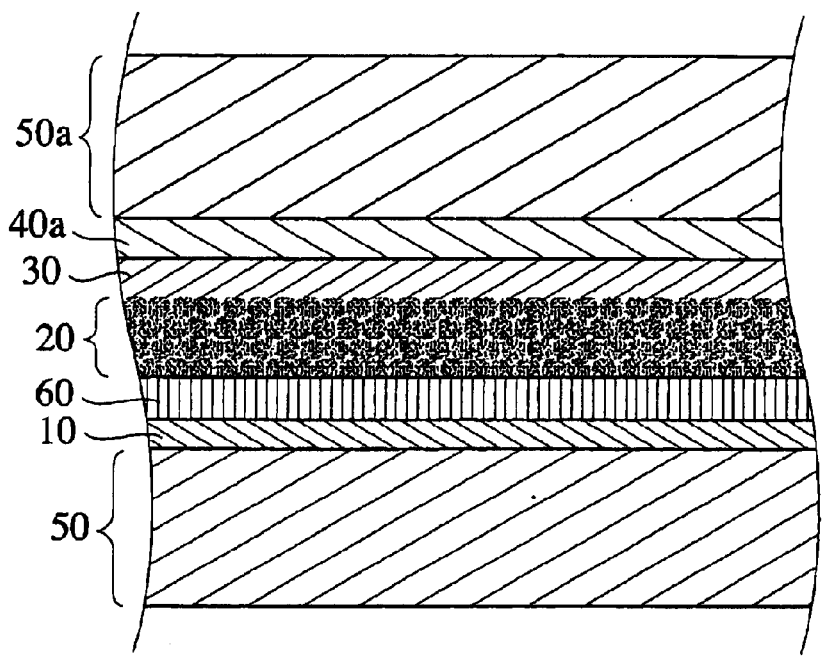
FIG. 7 is a partial cross sectional view showing a still further preferable structure of the photoelectric conversion device of the present invention.

In the structure illustrated in FIG. 7, a substrate 50 is provided with an electrically conductive layer 10, an undercoating layer 60, a photosensitive layer 20, a charge transfer layer 30 and a transparent counter electrode layer 40a in this order, and then attached to a transparent substrate 50a. This structure allows light incidence from the side of the counter electrode.

Figure 8:
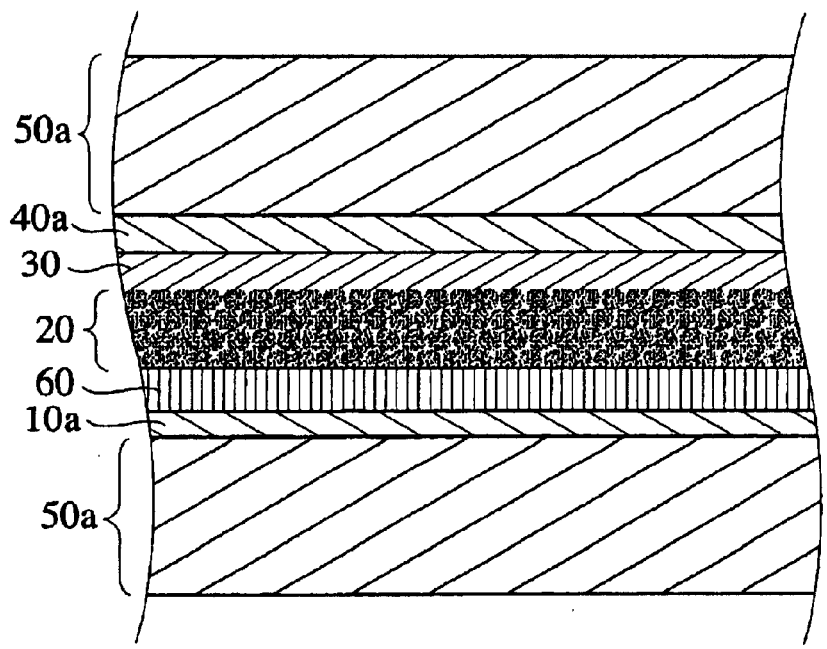
FIG. 8 is a partial cross sectional view showing a still further preferable structure of the photoelectric conversion device of the present invention.

In the structure illustrated in FIG. 8, a transparent substrate 50a is provided with an electrically conductive transparent layer 10a, an undercoating layer 60, a photosensitive layer 20, a charge transfer layer 30 and a transparent counter electrode layer 40a in this order, and then attached to a transparent substrate 50a. This structure allows light incidence from both sides of the photoelectric conversion device.

Figure 9:
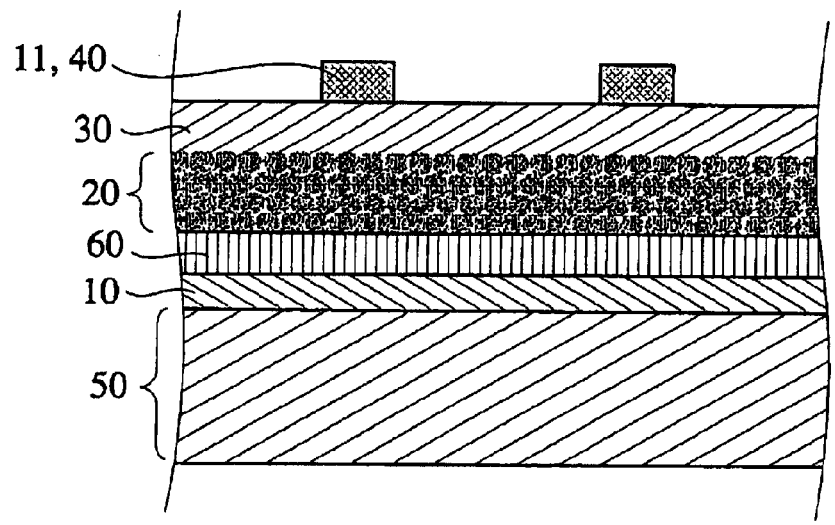
FIG. 9 is a partial cross sectional view showing a still further preferable structure of the photoelectric conversion device of the present invention.

In the structure illustrated in FIG. 9, a substrate 50 is provided with an electrically conductive layer 10, an undercoating layer 60, a photosensitive layer 20, a solid charge transfer layer 30 in this order, and then partially provided with a counter electrode layer 40 or a metal lead 11. This structure allows light incidence from the side of the counter electrode.

[3] Photoelectric Cell

The photoelectric cell of the present invention comprises the above photoelectric conversion device of the present invention to do job in an external circuit or generate electricity in the external circuit. Such a photoelectric cell that has the charge transfer layer comprising the ion-conductive electrolytic composition is generally referred to as a photoelectrochemical cell. The photoelectric cell intended for generating power with solar light is referred to as a solar cell.

The edges of the photoelectric cell are preferably sealed with a polymer or an adhesive, etc. to prevent the cell content from deteriorating and evaporating. A known external circuit may be connected to the conductive support and the counter electrode via a lead.

When the photoelectric conversion device of the present invention is used for a solar cell, the interior structure of the solar cell may be essentially the same as that of the photoelectric conversion device mentioned above. The solar cell comprising the photoelectric conversion device of the present invention may have a known module structure. In a general module structure of the solar cell, a cell is disposed on a substrate of metal, ceramic, etc. and covered with a packing resin, a protective glass, etc., whereby light is introduced from the opposite side of the substrate. The solar cell module may have a structure where the cell is placed on a substrate of a transparent material such as a tempered glass to introduce light from the transparent substrate side. Specifically, a superstraight-type module structure, a substrate-type module structure, a potting-type module structure, substrate-integrated module structure that is generally used in amorphous silicon solar cells, etc. are known as the solar cell module structure. The dye-sensitive solar cell of the present invention may have a module structure properly selected from the above structures depending on ends, locations and environment where it is used, and preferably has a module structure disclosed in JP 2000-268892 A.

The present invention will be explained in more detail with reference to Examples below without intention of restricting the scope of the present invention.

EXAMPLE 1

Synthesis of Basic Compound b2-1

A solution containing 6.8 ml of anhydrous trifluoromethane sulfonic acid and 50 ml of methylene chloride was slowly dropped into a solution containing 3.8 g of 3-aminopyridine, 5.7 ml of triethylamine and 50 ml of acetonitrile at −50° C. in a nitrogen atmosphere. The resultant reaction liquid was stirred for 1 hour without treatment, heated to room temperature, and further stirred for 1 hour. The resultant solution was then filtered and concentrated, and the resultant residue was purified with chromatography with a silica gel column to obtain 6.4 g of 3-trifluoromethane sulfonamide pyridine.

0.4 g of 3-trifluoromethane sulfonamide pyridine was dissolved in an aqueous solution containing 1.2 g of sodium hydroxide and 80 ml of water, to which an aqueous solution containing 4.6 g of silver nitrate and 20 ml of water was added. After stirring the reaction liquid at 40° C. for 2 hours, a precipitate formed in the reaction liquid was filtered out and washed with acetonitrile. The washed precipitate was added to 50 ml of acetonitrile, and an aqueous solution containing 2.7 g of 1-ethyl-3-methylimidazolium bromide and 50 ml of water was added thereto. After stirring the resultant mixture at 40° C. for 2 hours, the precipitated silver bromide was removed by filtration. The resultant filtrate was then concentrated, and the resultant residue was purified with chromatography with a silica gel column and dried by a vacuum pump to obtain 3.0 g of Basic Compound b2-1.

The resultant Basic Compound b2-1 was a low-viscosity liquid at room temperature. The structure of Basic Compound b2-1 was identified by $^1$H-NMR and mass spectrum. $^1$H-NMR peak shift values of Basic Compound b2-1 were as follows:

$^1$H-NMR (δ value, $(CD_3)_2SO$): 9.33 (s, 1H), 8.28 (s, 1H), 8.08 (d, 1H), 7.51 (d, 1H), 7.31 (s, 1H), 7.30 (s, 1H), 7.07 (dd, 1H), 4.09 (q, 2H), 3.89 (s, 3H), 1.49 (t, 3H).

EXAMPLE 2

1. Preparation of Titanium Dioxide Dispersion

A dispersion of titanium dioxide particles, whose concentration was 11% by mass, was prepared in the same manner as in the method described in Christophe J. Barb'e, et al, the Journal of American Ceramic Society, Vol. 80, No. 12, page 3157 (1997) except that an autoclave temperature was 230° C. The average particle diameter of the titanium dioxide particles in the dispersion was about 10 nm. Added to and mixed with this dispersion was polyethylene glycol (molecular weight: 20000, available from Wako Pure Chemical Industries, Ltd) in an amount of 20% by mass based on the titanium dioxide, to obtain a dispersion of titanium dioxide particles.

2. Preparation of Dye-Adsorbed Titanium Dioxide Electrode (1) Preparation of Dye-Adsorbed Electrode The above dispersion of titanium dioxide particles was applied to an electrically conductive, transparent glass coated with fluorine-doped tin oxide (surface resistance: approximately 10 $Ω/cm^2$, available from Nippon Sheet Glass Co., Ltd.,) on the conductive layer side at a thickness of 120 μm by a doctor blade, and dried at 25° C. for 30 minutes. Thereafter, it was burned at 450° C. for 30 minutes in an electric furnace "muffle furnace FP-32" available from YAMATO SCIENTIFIC CO., LTD., and cooled to form a titanium dioxide layer, resulting in a titanium dioxide electrode. The amount of titanium dioxide coated per a unit area (1 $m^2$) of the electrically conductive, transparent glass was 18 $g/m^2$, and the thickness of the titanium dioxide layer was 12 μm.

The resultant titanium dioxide electrode was immersed in a dye adsorption liquid containing a ruthenium complex dye R-1 in a mixed solvent of ethanol and acetonitrile (volume ratio of ethanol to acetonitrile was 1 to 1) at 25° C. for 16 hours, and washed with ethanol and acetonitrile successively to obtain a dye-adsorbed electrode T-1. Incidentally, the ruthenium complex dye R-1 was a cis-(dithiocyanate)-N,N'-bis(2,2'-bipyridyl-4,4'-dicarboxilic acid) ruthenium (II) complex, and the concentration of the ruthenium complex dye R-1 in the dye adsorption liquid was $3×10^{-4}$ mol/L.

A dye-adsorbed electrode D-1 was produced in the same manner as in the dye-adsorbed electrode T-1 except that LiI was added to the dye adsorption liquid at a concentration of 0.01 mol/L.

(2) Preparation of Treated Electrode

The dye-adsorbed electrode T-1 was immersed in either one of treating liquids AS-1 to AS-3 shown in Table 1 containing a treatment compound (a ureide compound or a silyl compound) at 40° C. for 1.5 hours, washed with acetonitrile, and dried in the dark in a nitrogen atmosphere to provide a treated electrode TA-1 to TA-3. The concentration of the treatment compound in the treating liquid was 0.01 mol/L, and a solvent for the treating liquid was acetonitrile. 4-methoxypyridine was added to the treating liquid as an additive at a concentration of 0.1 mol/L.

A treated electrode TA-4 was produced in the same manner as in the treated electrodes TA-1 to TA-3 except for using a treating liquid AS-4 containing only 4-methoxypyridine without a ureide compound or a silyl compound.

Treated electrodes DA-1 to DA-4 were produced in the same manner as in the treated electrodes TA-1 to TA-4, respectively, except for using a dye-adsorbed electrode D-1 in place of the dye-adsorbed electrode T-1.

TABLE 1

| Treated Electrode | Dye-Adsorbed Electrode | Treating Liquid | Treatment Compound | Additive in Treating Liquid |
|---|---|---|---|---|
| TA-1 | T-1 | AS-1 | A-5 | 4-methoxypyridine (0.1 mol/L) |
| TA-2 | T-1 | AS-2 | A-27 | 4-methoxypyridine (0.1 mol/L) |
| TA-3 | T-1 | AS-3 | A-6 | 4-methoxypyridine (0.1 mol/L) |
| TA-4 | T-1 | AS-4 | None | 4-methoxypyridine (0.1 mol/L) |
| DA-1 | D-1 | AS-1 | A-5 | 4-methoxypyridine (0.1 mol/L) |
| DA-2 | D-1 | AS-2 | A-27 | 4-methoxypyridine (0.1 mol/L) |
| DA-3 | D-1 | AS-3 | A-6 | 4-methoxypyridine (0.1 mol/L) |
| DA-4 | D-1 | AS-4 | None | 4-methoxypyridine (0.1 mol/L) |

3. Preparation of Charge Transfer Material 1 g of iodine was added to a mixture liquid containing 35 g of 1-methyl-3-propylimidazolium iodide (Y6-8) and 15 g of 1-ethyl-3-methyl imidazolium tetrafluoroborate (Y6-2) and dissolved therein by stirring to prepare a comparative charge transfer material MS-1. Added to 1 g of the comparative charge transfer material MS-1 was the basic compound (I) or a comparative compound, and/or an alkali metal salt or an alkaline earth metal salt shown in Table 2 in an amount shown in Table 2. The resultant mixture was stirred to have additives dissolved in a solvent, to prepare comparative charge transfer materials MS-2 to MS-5 and charge transfer materials MS-6 to MS-17 of the present invention. Any of the charge transfer materials MS-1 to MS-17 was liquid at room temperature.

TABLE 2

| Charge Transfer Material | Basic Compound (I) or Comparative Compound (amount) | ALKALI METAL Salt or Alkaline Earth Metal Salt (amount) |
|---|---|---|
| MS-1 | None | None |
| MS-2 | None | LiI (0.2 mmol) |
| MS-3 | 4-t-butylpyridine (0.05 mmol) | None |
| MS-4 | 4-t-butylpyridine (1 mmol) | LiI (0.2 mmol) |
| MS-5 | H-1 (1 mmol) | LiI (0.2 mmol) |
| MS-6 | b2-1 (0.05 mmol) | None |
| MS-7 | b2-1 (1 mmol) | LiI (0.2 mmol) |
| MS-8 | b2-1 (1 mmol) | Li(NSO$_2$CF$_3$)$_2$ (0.2 mmol) |
| MS-9 | b1-3 (1 mmol) | MgI$_2$ (0.2 mmol) |
| MS-10 | b3-1 (0.5 mmol) | LiI (0.2 mmol) |
| MS-11 | b3-2 (1 mmol) | LiI (0.2 mmol) |
| MS-12 | b3-3 (1 mmol) | LiI (0.2 mmol) |
| MS-13 | b4-1 (1 mmol) | LiI (0.2 mmol) |
| MS-14 | b1-9 (1 mmol) | LiI (0.2 mmol) |
| MS-15 | b2-6 (1 mmol) | LiI (0.2 mmol) |

TABLE 2-continued

| Charge Transfer Material | Basic Compound (I) or Comparative Compound (amount) | ALKALI METAL Salt or Alkaline Earth Metal Salt (amount) |
|---|---|---|
| MS-16 | b2-15 (0.5 mmol) | LiI (0.2 mmol) |
| MS-17 | b2-4 (1 mmol) | LiI (0.2 mmol) |

(H-1)

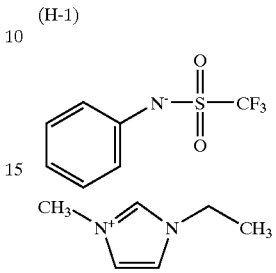

4. Production of Photoelectric Conversion Device

Figure 10:
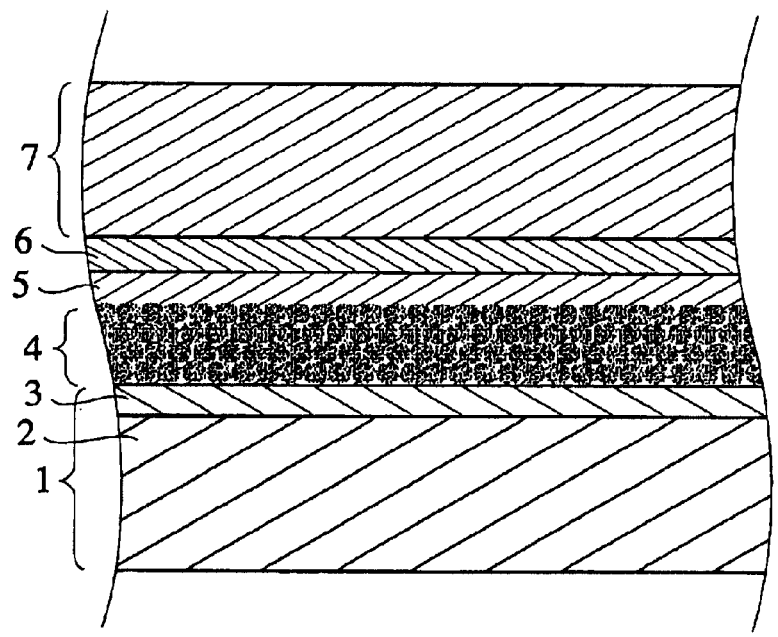
FIG. 10 is a partial cross sectional view showing a structure of a photoelectric conversion device produced in Examples.

A titanium dioxide layer was removed in a circular shape of 8 mm in diameter from the electrode T-1 of 2 cm×2 cm, and a 25-$\mu$m-thick thermoplastic resin of 1.5 cm×1.5 cm having a circular hole of 1 cm in diameter was placed thereon. They were integrated by pressing at 100° C. for 20 seconds. Thereafter, 10 $\mu$l of the comparative charge transfer material MS-1 was poured onto the titanium dioxide layer in the hole of the thermoplastic resin, and left to stand at 50° C. for 12 hours to cause the charge transfer material to penetrate into the dye-adsorbed titanium dioxide electrode. A platinum-deposited glass of 2 cm×3 cm was then laminated to these electrodes, and an overflowing excess charge transfer material was wiped out. Thereafter, pressing was carried out at 130° C. for 30 seconds to prepare a comparative photoelectric conversion device C-1. All of these operations were carried out in a dry room at a temperature of a dew point −50° C. or lower. The resultant photoelectric conversion device had a laminate structure comprising a conductive glass 1 constituted by a glass 2 and an electrically conductive layer 3 formed thereon, a dye-adsorbed titanium dioxide layer 4, a charge transfer layer 5, a platinum layer 6 and a glass 7 in this order, as shown in FIG. 10.

Comparative photoelectric conversion devices C-2 to C-5 and photoelectric conversion devices C-6 to C-26 of the present invention were produced in the same manner as in the comparative photoelectric conversion device C-1 except that the electrode and/or the charge transfer material was replaced by those shown in Table 3.

5. Measurement of Photoelectric Conversion Efficiency

A simulated sunlight was obtained by passing light of a 500-W xenon lamp available from USHIO INC. through an "AM 1.5 filter" available from Oriel. The simulated sunlight had intensity of 100 mW/cm$^2$ in a vertical plane. A silver paste was applied to an edge of an electrically conductive glass in each of the photoelectric conversion devices C-1 to C-26 to form a negative electrode, and the negative electrode and a platinum-deposited glass as a positive electrode were connected to a current-voltage tester "Keithley SMU238." While vertically irradiating the simulated sunlight to each photoelectric conversion device, its current-voltage characteristics were measured to determine its photoelectric conversion efficiency. The photoelectric conversion efficiency of each of the comparative photoelectric conversion devices C-1 to C-5 and the photoelectric conversion devices C-6 to C-26 of the present invention is shown in Table 3.

To evaluate the long-period storage stability of each photoelectric conversion device, each photoelectric conversion device was stored in a constant-temperature, constant-humidity chamber under the conditions of a temperature of 60° C. and a humidity of 50% for 3 months, to measure photoelectric conversion efficiency in the same manner. The results are also shown in Table 3.

TABLE 3

| Photoelectric Conversion Device | Electrode | Charge Transfer Material | Photoelectric Conversion Efficiency (%) | | Decrease[1] |
|---|---|---|---|---|---|
| | | | Initial | After 3-month Storage | |
| C-1 | T-1 | MS-1 | 4.3 | 4.1 | 0.2 |
| C-2 | T-1 | MS-2 | 3.0 | 2.6 | 0.4 |
| C-3 | T-1 | MS-3 | 4.9 | 3.9 | 1.0 |
| C-4 | T-1 | MS-4 | 5.2 | 4.1 | 0.9 |
| C-5 | T-1 | MS-5 | 3.7 | 3.5 | 0.2 |
| C-6 | T-1 | MS-6 | 5.0 | 4.9 | 0.1 |
| C-7 | T-1 | MS-7 | 5.8 | 5.6 | 0.2 |
| C-8 | T-1 | MS-8 | 5.7 | 5.6 | 0.1 |
| C-9 | T-1 | MS-9 | 4.7 | 4.6 | 0.1 |
| C-10 | T-1 | MS-10 | 5.7 | 5.5 | 0.2 |
| C-11 | T-1 | MS-11 | 5.2 | 5.0 | 0.2 |
| C-12 | T-1 | MS-12 | 4.9 | 4.3 | 0.6 |
| C-13 | T-1 | MS-13 | 5.1 | 5.0 | 0.1 |
| C-14 | T-1 | MS-14 | 4.8 | 4.4 | 0.4 |
| C-15 | T-1 | MS-15 | 5.3 | 5.2 | 0.1 |
| C-16 | T-1 | MS-16 | 5.5 | 5.2 | 0.3 |
| C-17 | T-1 | MS-17 | 5.6 | 5.4 | 0.2 |
| C-18 | D-1 | MS-7 | 5.3 | 4.9 | 0.2 |
| C-19 | TA-1 | MS-7 | 6.0 | 5.8 | 0.2 |
| C-20 | TA-2 | MS-7 | 5.9 | 5.7 | 0.2 |
| C-21 | TA-3 | MS-7 | 6.4 | 6.1 | 0.3 |
| C-22 | TA-4 | MS-7 | 5.9 | 5.6 | 0.3 |
| C-23 | DA-1 | MS-7 | 6.0 | 5.7 | 0.3 |
| C-24 | DA-2 | MS-7 | 6.2 | 5.9 | 0.3 |
| C-25 | DA-3 | MS-7 | 6.8 | 6.7 | 0.1 |
| C-26 | DA-4 | MS-7 | 5.0 | 4.9 | 0.1 |

Note
[1]Decrease from the initial photoelectric conversion efficiency to that after 3-month storage.

As shown in Table 3, the photoelectric conversion devices C-6 to C-26 of the present invention using the charge transfer material of the present invention comprising the basic compound (I) are excellent in photoelectric conversion efficiency, as compared with the comparative photoelectric conversion devices C-1 and C-2 using the charge transfer material comprising no basic compound having negative charge, and the comparative photoelectric conversion device C-5 using a comparative compound H-1 comprising no basic group.

Though the comparative photoelectric conversion devices C-3 and C-4 using the charge transfer material comprising 4-t-butylpyridine exhibited excellent photoelectric conversion efficiency immediately after their production, their photoelectric conversion efficiency drastically decreased by long-term storage, proving that the photoelectric conversion devices C-6 to C-26 of the present invention are excellent in durability.

The comparison of the photoelectric conversion devices C-12 and C-14 of the present invention with the photoelectric conversion devices C-6 to C-11, C-13 and C-15 to C-17 has revealed that the basic compound (I) having negative charge on a nitrogen atom is preferable from the viewpoint of durability. Further, the comparison of the photoelectric conversion device C-7 with the photoelectric conversion devices C-15 and C-17 in photoelectric conversion efficiency and durability has revealed that basic compounds containing trifluoromethane sulfonamide anion are particularly preferable among those having substituents with negative charge on a nitrogen atom. In addition, the comparison of the photoelectric conversion device C-6 of the present invention with the photoelectric conversion devices C-7 and C-8 of the present invention has revealed that it is preferable from the viewpoint of photoelectric conversion efficiency to use an alkali metal salt together with the basic compound (I).

Further, the comparison of the photoelectric conversion device C-7 of the present invention with the photoelectric conversion devices C-19 to C-22 of the present invention has revealed that the treatment of the layer of dye-adsorbed, fine semiconductor particles with a ureide compound and/or a silyl compound improves the photoelectric conversion efficiency of the photoelectric conversion device. Further, the comparison of the photoelectric conversion devices C-19 to C-21 of the present invention with the photoelectric conversion devices C-23 to C-25 of the present invention has revealed that in the treatment with a ureide compound and/or a silyl compound, it is preferable from the viewpoint of photoelectric conversion efficiency to add an alkali metal salt to a dye-adsorbing liquid.

EXAMPLE 3

Dye-adsorbed electrodes T-2 to T-4 were produced in the same manner as in the dye-adsorbed electrode T-1 except that ruthenium complex dye R-10, merocyanine dye M-3 or squarylium dye M-1 was used in place of the ruthenium complex dye R-1. The concentration of the dye in the dye adsorption liquid was $1 \times 10^{-4}$ mol/L. With the dye-adsorbed electrodes T-2 to T-4 and the charge transfer materials shown in Table 4, comparative photoelectric conversion devices C-27, C-28, C-30, C-31, C-33 and C-34 and photoelectric conversion devices C-29, C-32 and C-35 of the present invention were produced in the same manner as in Example 2. The photoelectric conversion efficiency and durability of each photoelectric conversion device were evaluated in the same manner as in Example 2, providing the same results as in Example 2, as shown in Table 4.

TABLE 4

| Photoelectric Conversion Device | Electrode | Dye | Charge Transfer Material | Photoelectric Conversion Efficiency (%) | | Decrease[1] |
|---|---|---|---|---|---|---|
| | | | | Initial | After 3-month Storage | |
| C-27 | T-2 | R-10 | MS-1 | 4.0 | 3.6 | 0.4 |
| C-28 | T-2 | R-10 | MS-4 | 4.7 | 3.5 | 0.8 |
| C-29 | T-2 | R-10 | MS-6 | 5.6 | 5.3 | 0.3 |
| C-30 | T-3 | M-3 | MS-1 | 3.4 | 2.8 | 0.6 |
| C-31 | T-3 | M-3 | MS-4 | 3.8 | 1.9 | 1.9 |
| C-32 | T-3 | M-3 | MS-6 | 4.3 | 3.9 | 0.4 |
| C-33 | T-4 | M-1 | MS-1 | 3.2 | 2.5 | 0.7 |
| C-34 | T-4 | M-1 | MS-4 | 3.9 | 2.4 | 1.5 |
| C-35 | T-4 | M-1 | MS-6 | 4.4 | 3.6 | 0.8 |

Note
[1]Decrease from the initial photoelectric conversion efficiency to that after 3-month storage.

As explained above in detail, the dye-sensitized photoelectric conversion device using the charge transfer material of the present invention exhibits excellent photoelectric conversion efficiency. Because the basic compound (I) used in the present invention is nonvolatile, the charge transfer material containing this basic compound (I) is not likely to be depleted for a long period of use, so that the photoelectric conversion device using such charge transfer material can maintain high photoelectric conversion efficiency for a long period of time. In addition, by treating the layer of fine semiconductor particles with a ureide compound or an alkali metal salt in advance, the photoelectric conversion efficiency of the dye-sensitized photoelectric conversion device of the present invention is further improved.

What is claimed is:

1. A photoelectric conversion device comprising a conductive support, a layer of dye-adsorbed, fine semiconductor particles, a charge transfer layer and a counter electrode, said charge transfer layer comprising a charge transfer material comprising a basic compound having negative charge and represented by the following general formula (I):

$(A_1-L)_{n1}-A_2 \cdot M$          (1), wherein $A_1$ represents a group having negative charge; $A_2$ represents a basic group; M represents a cation for neutralizing the negative charge of $(A_1-L)_{n1}-A_2$; L represents a divalent linking group or a single bond; and n1 represents an integer of 1 to 3, wherein said $A_2$ is a pyridyl group or an imidazolyl group, and wherein said basic compound is in a molten state at room temperature.

2. The photoelectric conversion device according to claim 1, wherein said M in said charge transfer material comprising said basic compound is an alkali metal cation, an alkaline earth metal cation, a quaternary ammonium cation, an imidazolium cation or a pyridinium cation.

3. The photoelectric conversion device according to claim 1, wherein said $A_1$ in said charge transfer material comprising said basic compound is $R_1SO_2N^-$—, wherein $R_1$ represents an alkyl group having at least one fluorine substituent; said $A_2$ is a pyridyl group; said M is a lithium cation or an imidazolium cation; said L is a single bond; and said n1 is 1.

4. A photo-electrochemical cell comprising said photoelectric conversion device recited in claim 1.

5. The photoelectric conversion device according to claim 1, wherein said $A_1$ in said charge transfer material comprising said basic compound is $R_1SO_2N^-$—, wherein $R_1$ represents an alkyl group having at least one fluorine substituent; said 2 is a pyridyl group substituted by a fluorinated alkylsulfoneamide anion at the 3-position thereof; said M is an imidazolium cation; said L is a single bond; and said n1 is 1.

6. The photoelectric conversion device according to claim 1, wherein said semiconductor particles are particles of $TiO_2$.

7. The photoelectric conversion device according to claim 1, wherein said semiconductor particles are particles of $TiO_2$ pretreated with a ureide compound and/or a silyl compound.

8. A pyridine compound in a molten state at room temperature, which is an imidazolium salt of a pyridine substituted by a fluorinated alkylsulfonamide anion at the 3-position thereof.

* * * * *